United States Patent
An et al.

(10) Patent No.: US 12,343,405 B2
(45) Date of Patent: *Jul. 1, 2025

(54) HIGH STEROL-CONTAINING LIPID NANOPARTICLES

(71) Applicant: NanoVation Therapeutics Inc., Vancouver (CA)

(72) Inventors: Kevin An, Vancouver (CA); Daniel Kurek, Vancouver (CA); Jayesh Kulkarni, Vancouver (CA); Dominik Witzigmann, Vancouver (CA)

(73) Assignee: Nano Vation Therapeutics Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/599,893

(22) Filed: Mar. 8, 2024

(65) Prior Publication Data

US 2024/0207439 A1 Jun. 27, 2024

Related U.S. Application Data

(62) Division of application No. 18/187,904, filed on Mar. 22, 2023, now Pat. No. 11,951,177.

(Continued)

(51) Int. Cl.
*A61K 47/69* (2017.01)
*A61K 31/575* (2006.01)
(Continued)

(52) U.S. Cl.
CPC ........ *A61K 47/6909* (2017.08); *A61K 31/575* (2013.01); *A61K 31/661* (2013.01); *C12N 15/113* (2013.01)

(58) Field of Classification Search
CPC .............. A61K 47/6909; A61K 31/575; A61K 31/661; C12N 15/113
See application file for complete search history.

(56) References Cited

U.S. PATENT DOCUMENTS 5,041,278 A 8/1991 Janoff et al.
5,830,499 A 11/1998 Bouwstra
(Continued)

FOREIGN PATENT DOCUMENTS

CA 1337332 C 10/1995
CA 3088321 A1 8/2019
(Continued)

OTHER PUBLICATIONS

Bach, D., and Wachtel, E., "Phospholipid/cholesterol model membranes: formation of cholesterol crystallites", Biochimica et Biophysica Acta 1610 (2003) 187-197.

(Continued)

*Primary Examiner* — Blessing M Fubara
(74) *Attorney, Agent, or Firm* — Knobbe Martens Olson & Bear LLP

(57) ABSTRACT

The present disclosure provides a lipid nanoparticle comprising: a nucleic acid cargo molecule; sterol or a derivative thereof present at elevated content; neutral lipid; an ionizable lipid; and a hydrophilic polymer-lipid conjugate present at a content between 0.5 and 3 mol %, wherein each mol % content is relative to total lipid present in the lipid nanoparticle.

10 Claims, 18 Drawing Sheets

Related U.S. Application Data

(60) Provisional application No. 63/269,815, filed on Mar. 23, 2022.

(51) Int. Cl.
*A61K 31/661* (2006.01)
*C12N 15/113* (2010.01)

(56) References Cited

U.S. PATENT DOCUMENTS

| | | | |
|---|---|---|---|
| 7,220,833 | B2 | 5/2007 | Nelson et al. |
| 7,514,099 | B2 | 4/2009 | Chen et al. |
| 8,058,069 | B2 | 11/2011 | Yaworski et al. |
| 8,492,359 | B2 | 7/2013 | Yaworski et al. |
| 8,822,668 | B2 | 9/2014 | Yaworski et al. |
| 9,301,923 | B2 | 4/2016 | Baryza et al. |
| 9,364,435 | B2 | 6/2016 | Yaworski et al. |
| 9,878,042 | B2 | 1/2018 | Yaworski et al. |
| 10,228,371 | B2 | 3/2019 | Baumeister et al. |
| 11,052,052 | B2 | 7/2021 | Schentag et al. |
| 11,141,378 | B2 | 10/2021 | Yaworski et al. |
| 11,191,849 | B2 * | 12/2021 | Abrams ............... A61K 47/544 |
| 11,219,634 | B2 | 1/2022 | Prieve et al. |
| 11,229,609 | B2 | 1/2022 | Cheng et al. |
| 11,291,734 | B2 | 4/2022 | Guild et al. |
| 11,338,044 | B2 | 5/2022 | Guild et al. |
| 11,547,754 | B2 | 1/2023 | Guild et al. |
| 12,011,507 | B2 * | 6/2024 | Kurek ................... C12N 15/88 |
| 2005/0037200 | A1 | 2/2005 | Wallach |
| 2010/0297242 | A1 | 11/2010 | Park et al. |
| 2011/0111044 | A1 | 5/2011 | Zhao et al. |
| 2011/0177156 | A1 | 7/2011 | Szoka, Jr. et al. |
| 2012/0308663 | A1 | 12/2012 | Roger |
| 2015/0140069 | A1 | 5/2015 | Hong et al. |
| 2019/0314291 | A1 | 10/2019 | Besin et al. |
| 2020/0078313 | A1 | 3/2020 | Roy et al. |
| 2020/0129445 | A1 | 4/2020 | Patel et al. |
| 2021/0267895 | A1 | 9/2021 | Yaworski et al. |
| 2021/0346306 | A1 | 11/2021 | Dimitrov et al. |
| 2023/0302153 | A1 | 9/2023 | An et al. |

FOREIGN PATENT DOCUMENTS

| | | |
|---|---|---|
| CA | 3158293 A1 | 5/2021 |
| WO | WO 2019/067992 A1 | 4/2019 |
| WO | WO 2019/141814 A1 | 7/2019 |
| WO | WO 2021/055892 A1 | 3/2021 |
| WO | WO 2021/163002 A1 | 8/2021 |

OTHER PUBLICATIONS

Brockerhoff and Ramsammy, "Preparation and Structural Studies of Cholesterol Bilayers", Biochimica et Biophysica Acta, 1982, 691:227-232.
Cheng and Lee, "The role of helper lipids in lipid nanoparticles (LNPs) designed for oligonucleotide delivery", Advanced Drug Delivery Reviews, 2016, 99:129-137.
Cheng et al., "Selective Organ Targeting (SORT) nanoparticles for tissue specific mRNA delivery and CRISPR/Cas Jene editing", Nat. Nanotechnol., Apr. 2020, 15(4): 313-320.
Dabkowska et al., "The effect of neutral helper lipids on the structure of cationic lipid monolayers", J_ R. Soc. interface, 2012, 9:548-561.
Drummond et al., "Optimizing Liposomes for Delivery of Chemotherapeutic Agents to Solid Tumors", Pharmacological Reviews, 1999, 51(4):691-743.
Foglia et al., "Structural Studies of the Monolayers and Bilayers Formed by a Novel Cholesterol- Phospholipid; chimera", Langmuir, 2011, 27:8275-8281.
Hayes et al., "Genospheres: self-assembling nucleic acid-lipid nanoparticles suitable for targeted gene delivery", 3ene Therapy, 2006, 13:646-651.
Huang and Szoka, "Sterol-Modified Phospholipids: Cholesterol and Phospholipid Chimeras with Improved Biomembrane Properties", J. Am. Chem. Soc., 2008, 130:15702-15712.
Huang et al., "Disterolphospholipids: Nonexchangeable Lipids and Their Application to Liposomal Drug Delivery", unchristen Agnew Chem., 2009, 121:4210-4213.
Man et al., "Characterization of the colloidal properties, in vitro antifungal activity, antileishmanial activity and toxicity n mice of a distagmasterylhemisuccinoyl-glycero-phosphocholine liposome-intercalated amphotericin B", International Journal of Pharmaceutics, 2011, 408:163-172.
Kieler-Ferguson et al., "Encapsulation, controlled release, and anti-tumor efficacy of cisplatin delivered in liposomes composed of sterol-modified phospholipids", European Journal of Pharmaceutical Sciences, 2017, 103:85-93.
Kubota et al., "Effect of the nanoformulation of siRNA-lipid assemblies on their cellular uptake and immune stimulation", International Journal of Nanomedicine, 2017, 12:5121-5133.
Kulkarni et al., "Lipid nanoparticles enabling gene therapies: from concepts to clinical utility", Nucleic Acid Therapeutics, 2018, 28(3):146-157.
Kulkarni et al., "On the Formation and Morphology of Lipid Nanoparticles Containing ionizable Cationic Lipids and iRNA", ACS Nano, 2018, 12:4787-4795.
Kulkarni et al., "On the role of helper lipids in lipid nanoparticle formulations of siRNA", Nanoscale, 2019, 11:21733-21739.
Patel et al., "Naturally—Occurring cholesterol analogues in lipid nanoparticles induce polymorphic shape and enhance intracellular delivery of mRNA", Nature Communications, 2020, 11(1):3435.
Pozzi et al., "Transfection efficiency boost of cholesterol-containing lipoplexes", Biochimica et Biophysica Acta, 2012, 1818:2335-2343.
Ramsammy et al., "Association of Cholesterol with Lysophosphatidylcholine", Chemistry and Physics of Lipids, 1983, 32:83-89.
Roces et al., "Manufacturing considerations for the development of lipid nanoparticles using microfluidics", Pharmaceutics, 2020, 12:1095.
Sakurai et al., "Effects of erythrocytes and serum proteins on lung accumulation of lipoplexes containing cholesterol Jr DOPE as a helper lipid in the single-pass rat lung perfusion system", European Journal of Pharmaceutics and Biopharmaceutics, 2001, 52:165-172.
Sato et al., "Hydrophobic scaffolds of pH-sensitive cationic lipids contribute to miscibility with phospholipids and improve the efficiency of delivering short interfering RNA by small-sized lipid nanoparticles", Acta Biomaterialia, 2020, 102:341-350.
Tenchov et al., "Cubic Phases in Phosphatidylcholine-cholesterol mixtures: Cholesterol as Membrane 'Fusogen'", Biophysical Journal, 2006, 91:2508-2516.
Written Opinion and International Search Report of the PCT, for PCT international application No. PCT/CA2023/050370, dated May 30, 2023, Issued by the Canadian Intellectual Property Office acting as the International Searching Authority of the PCT.
Yoshioka et al., "Cationic liposomes-mediated plasmid DNA delivery in murine hepatitis induced by carbon tetrachloride", Journal of Liposome Research, 2009, 19(2):141-147.
Yuan et al., "Ternary nanoparticles of anionic lipid nanoparticles/protamine/DNA for gene delivery", Int J Pharm, 2010, 392 (1-2):224-31.
Zhang et al., "Helper lipid structure influences protein adsorption and delivery of lipid nanoparticles to spleen and liver", Biomater. Sci., 2021, 9:1449-1463.
Zhang et al., "Helper lipid structure influences protein adsorption and delivery of lipid nanoparticles to spleen and liver", Biomater. Sci., 2021, 9:1449-1463, Supplementary Information.
Office Action issued in U.S. Appl. No. 18/187,904 dated Sep. 21, 2023.

* cited by examiner

HIGH STEROL-CONTAINING LIPID NANOPARTICLES

INCORPORATION BY REFERENCE TO PRIORITY APPLICATION

This application is a divisional of U.S. application Ser. No. 18/187,904, filed on Mar. 22, 2023, which claims priority to U.S. Provisional Application Ser. No. 63/269,815, filed on Mar. 23, 2022, each of which are hereby expressly incorporated herein by reference in their entirety.

TECHNICAL FIELD

The present disclosure relates to lipid nanoparticle formulations for the delivery of cargo such as nucleic acid.

BACKGROUND

Lipid nanoparticle (LNP) formulations represent a revolution in the field of nucleic acid delivery. An early example of a lipid nanoparticle product approved for clinical use is Onpattro™ Onpattro™ is a lipid nanoparticle-based short interfering RNA (siRNA) drug for the treatment of polyneuropathies induced by hereditary transthyretin amyloidosis. The success of this LNP delivery system paved the way for the clinical development of the leading LNP-based COVID-19 mRNA vaccines.

The Onpattro™ LNP formulation consists of four main lipid components, namely: ionizable amino lipid, distearoylphosphatidylcholine (DSPC), cholesterol, and polyethylene glycol conjugated lipids (PEG-lipids) at respective molar amounts of 50/10/38.5/1.5. Onpattro™ is still considered the gold standard for comparison in studies of LNP-mediated efficacy and current approaches to LNP design make few deviations from the four-component system.

Of these four components, the ionizable cationic lipid is considered important for the in vitro and in vivo activity of the LNP system. Accordingly, most work in the field has focused primarily on improving this lipid component. The ionizable cationic lipid is typically positively charged at low pH, which facilitates association with the negatively charged nucleic acid but is neutral at physiological pH, making it more biocompatible in biological systems. Further, it has been suggested that after the lipid nanoparticles are taken up by a cell by endocytosis, the ability of these lipids to ionize at low pH enables endosomal escape. This in turn allows the nucleic acid to be released into the intracellular compartment.

The ionizable cationic lipid is present at 50 mol % (relative to total lipid in the LNP) and thus makes up the bulk of the Onpattro™ formulation. With respect to the remaining three lipid components, the PEG-lipid is well known for preventing aggregation of the LNP and cholesterol functions to stabilize the particle. DSPC is a bilayer-forming lipid and it is generally accepted that it has an essential structural role in the LNP membrane.

Reports suggest that DSPC and cholesterol in empty Onpattro™-type LNP systems reside in outer lipid layers but that in systems loaded with siRNA, the DSPC and cholesterol is internalised together with siRNA in a hydrophobic core. At low levels of both components (lower than 40 mol % combined DSPC and cholesterol content) the siRNA encapsulation efficiency was progressively reduced (Kulkarni et al., 2019, Nanoscale, 11:21733-21739). It was concluded that the presence of both DSPC and cholesterol is vital to the stable encapsulation of siRNA in the LNP. The studies only investigated LNPs having a cholesterol content of up to 40 mol % (1:1 chol/DSPC) due to concerns regarding the solubility of cholesterol. It was stated that other studies have shown that cholesterol is known to have limited solubility in ionizable cationic lipid above pH 7.4. It has been suggested that DSPC is required to stably retain cholesterol and LNP formulations beyond 40:40 of chol/DSPC (mol/mol) were not investigated to avoid ambiguities resulting from the presence of excess cholesterol.

Other studies have investigated the effect of cholesterol on two-component lipoplex systems containing ionizable cationic lipid and cholesterol, but these studies used a 1:1 molar ratio of the two lipid components and did not examine the impact of raising the cholesterol content, such as above 50 mol % (Cheng and Lee, 2016, Advanced Drug Delivery Reviews, 99:129-137; Sakurai et al., 2001, European Journal of Pharmaceutics and Biopharmaceutics, 52:165-172; Dabkowska et al., 2012, J. R. Soc. Interface, 9:548-561; Yoshioka et al., 2009, Journal of Liposome Research, 19(2): 141-147). Other studies have examined the effect of cholesterol on lipoplexes to form cubic phases, but the lipid dispersions formed (using thin film hydration) contained high levels of phospholipid (Tenchov et al., 2006, Biophysical Journal, 91: 2508-2516).

Studies conducted in vivo that examined large unilamellar liposomes (LUVs) containing phospholipid/cholesterol found that cholesterol increased the circulation lifetimes of the LUVs, but the impact of cholesterol on increasing circulation lifetime plateaued at 30 mol % (Semple et al., 1996, Biochemistry, 35(8):2521-2525).

U.S. Pat. No. 11,191,849 discloses mRNA-LNPs having 55 mol % ionizable cationic lipid, 41 mol % cholesterol and 3.3 mol % PEG2000-C-DMA. Inflammatory responses after administration of the LNP in mice were reduced compared to the base composition (PEG-2000-C-DMA/cationic lipid/cholesterol/DSPC at 1.6/55/33/11 mol %) without impacting potency. The results observed were attributed in part to a higher than usual PEG-lipid conjugate content (>3 mol %).

Despite the foregoing advances in the art, there is a continuing need for LNP formulations that have desirable properties for the delivery of nucleic acids.

SUMMARY

The present disclosure addresses one or more problems in the art and/or provides useful alternatives thereof.

The present disclosure is based in part on the finding that LNPs with elevated sterol content and low levels of ionizable lipid relative to the Onpattro™ LNP (e.g., significantly greater than 38.5 mol % sterol, such as cholesterol) possess high nucleic acid encapsulation efficiencies. Furthermore, the LNPs described herein have been found to exhibit comparable in vitro and in vivo nucleic acid delivery potency as Onpattro™ LNP, despite these significant departures in lipid composition from the "gold standard" benchmark.

In one example of the disclosure, the LNPs having high levels of sterol or a derivative thereof exhibit improved targeting to the liver over the spleen. In some embodiments, targeting to the liver over the spleen is improved relative to an Onpattro™ LNP.

According to one embodiment of the disclosure, there is provided a lipid nanoparticle comprising: a nucleic acid cargo molecule; a sterol or a derivative thereof present at a content between 49 mol % and 85 mol %; substantially no phospholipid; an ionizable lipid; and a hydrophilic polymer—lipid conjugate present at a content between 0.5 and 3 mol %, wherein each mol % content is relative to total lipid present in the lipid nanoparticle.

In one embodiment, the sterol or the derivative thereof is present at a content of at least 50 mol % and/or the ionizable lipid is present at a content that is less than 48.5 mol %.

In another embodiment, the sterol or the derivative thereof is present at a content of at least 52 mol % and/or the ionizable lipid is present at a content that is less than 46.5 mol %.

In a further embodiment, the sterol or the derivative thereof is present at a content of at least 54 mol % and/or the ionizable lipid is present at a content that is less than 44.5 mol %.

In another embodiment, the sterol or the derivative thereof is present at a content of at least 56 mol % and/or the ionizable lipid is present at a content that is less than 42.5 mol %.

In a further embodiment, the sterol or the derivative thereof is present at a content of at least 58 mol % and/or the ionizable lipid is present at a content that is less than 40.5 mol %.

In another embodiment, the sterol or the derivative thereof is present at a content of at least 60 mol % and/or the ionizable lipid is present at a content that is less than 38.5 mol %.

In a further embodiment, the sterol or the derivative thereof is present at a content of at least 62 mol % and/or the ionizable lipid is present at a content that is less than 36.5 mol %.

In a further embodiment, the sterol or the derivative thereof is present at a content of at least 63 mol % and/or the ionizable lipid is present at a content that is less than 35.5 mol %.

In another embodiment, the sterol or the derivative thereof is present at a content of at least 64 mol % and/or the ionizable lipid is present at a content that is less than 34.5 mol %.

In a further embodiment, the sterol or the derivative thereof is present at a content of at least 65 mol % and/or the ionizable lipid is present at a content that is less than 33.5 mol %.

In yet another embodiment, the sterol or the derivative thereof is present at a content of at least 66 mol % and/or the ionizable lipid is present at a content that is less than 32.5 mol %.

In one embodiment, the phospholipid content is less than 1 mol %. In another embodiment, the phospholipid content is less than 0.5 mol %.

In a further embodiment, the hydrophilic-polymer lipid content is less than 2.5 mol %.

In one embodiment, the cargo molecule is siRNA, mRNA, vector nucleic acid, an antisense oligonucleotide or is a nucleic acid-protein or peptide complex.

In a further embodiment, the cargo molecule is siRNA, vector nucleic acid or an antisense oligonucleotide.

In another embodiment, the ionizable lipid is an amino lipid.

In yet a further embodiment, the sterol derivative is a non-cationic lipid.

In a further embodiment, the lipid nanoparticle has an electron dense core as visualized by cryo-TEM.

In a further embodiment, the lipid nanoparticle has substantially no neutral lipid.

In another embodiment, the sterol is cholesterol or the sterol derivative is a cholesterol derivative.

In a further embodiment, the lipid nanoparticle further comprises a tocopherol. For example, the tocopherol may be present at between 0.5 and 15 mol %.

According to another aspect of the disclosure, there is provided a method for delivery of mRNA or vector DNA for in vivo production of a protein or peptide in the liver, the method comprising administering to a mammal a lipid nanoparticle having at least 45 mol % of a sterol or a derivative thereof, a neutral lipid and an ionizable lipid, wherein the mRNA or vector DNA is encapsulated within the lipid nanoparticle and wherein the administering of the lipid nanoparticle results in liver-specific expression of the protein or peptide encoded by the mRNA or vector DNA, wherein the lipid nanoparticle has increased expression of the protein or peptide encoded by the mRNA or vector DNA in the liver over the spleen by at least 20-fold.

According to another aspect, there is provided a method for delivery of siRNA or antisense oligonucleotide for in vivo silencing of a gene in the liver, the method comprising administering to a mammal a lipid nanoparticle having at least 45 mol % of a sterol or a derivative thereof, a neutral lipid and an ionizable lipid, wherein the mRNA is encapsulated within the lipid nanoparticle and wherein the administering of the lipid nanoparticle results in liver-specific silencing of the protein or peptide encoded by a nucleic acid sequence, wherein the lipid nanoparticle has an increase in silencing of the nucleic acid in the liver over the spleen by at least 5-fold.

According to one embodiment of the disclosure, the increased expression of the protein or peptide encoded by the mRNA in the liver over the spleen is at least 10% greater than the increased expression in an Onpattro LNP in the liver over the spleen.

According to a further embodiment, the neutral lipid content is between 0 and 10 mol %. In one example of the disclosure, the neutral lipid content is less than 8 mol %, 7 mol %, 6 mol %, 5 mol % or 4 mol %.

According to another embodiment, the sterol or derivative thereof is present at 45 to 80 mol %.

According to another embodiment, the sterol or derivative thereof is present at 49 to 65 mol %.

According to a further embodiment, a hydrophilic polymer-lipid conjugate present in the lipid nanoparticle at a content between 0.5 and 3 mol %.

According to one embodiment, the ionizable lipid component in any of the foregoing aspects and/or embodiments includes a mixture of ionizable cationic lipid and an ionizable anionic lipid.

DETAILED DESCRIPTION

Sterol or Sterol Derivative

Figure 1:
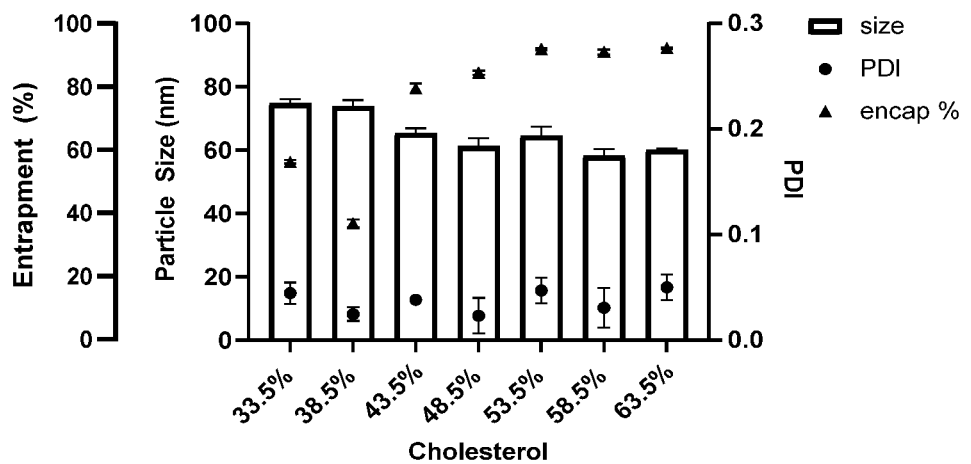
FIG. 1 is a graph showing encapsulation efficiency (%), particle size (nm) and polydispersity index (PDI) of lipid nanoparticle (LNP) formulations DLin-MC3-DMA (MC3) ionizable lipid/cholesterol/PEG-DMG at respective mol % ratios of X/98.5-X/1.5 encapsulating anti-sense oligonucleotide targeting c-myc as a function of increasing cholesterol content. The cholesterol content was increased from 33.5 mol % to 63.5 mol %. The nitrogen-to-phosphate (N/P) ratio was 3.

At set forth herein, the LNPs of the disclosure have sterol or sterol derivative levels that significantly exceed those used in conventional four-component Onpattro™_like formulations for nucleic acid delivery.

The term "sterol" refers to steroids that are naturally-occurring or synthetic. The term includes phytosterols, zoosterols and derivatives thereof.

The term "sterol derivatives" refers to modified sterols or precursors thereof, including triterpenes.

The term "cholesterol" refers to a naturally-occurring or synthetic compound having a gonane skeleton and that has a hydroxyl moiety attached to one of its rings, typically the A-ring.

The LNP may alternatively or additionally comprise a "cholesterol derivative". The cholesterol derivative may be naturally-occurring or man-made and includes but is not limited to a cholesterol molecule having a gonane structure and one or more additional functional groups.

In another embodiment, the LNP may comprise a triterpene. Non-limiting examples include squalene, achilleol A, polypodatetraene, malabaricane, lanostane, cucuribitacin, hopane, oleanane, and urosolic acid.

The LNP may further comprise a tocopherol as an additional component. In certain embodiments, the cholesterol derivative is a phytosterol. The phytosterol may be β-sitosterol, 3-sitosterol, campesterol, stigmasterol, fucosterol, or stigmastanol or a salt or ester thereof.

In certain embodiments, the cholesterol derivative is selected from β-sitosterol, β-sitosterol acetate, 3-sitosterol, campesterol, stigmasterol, fucosterol, or stigmastanol, dihydrocholesterol, ent-cholesterol, epi-cholesterol, desmosterol, cholestanol, cholestanone, cholestenone, cholesteryl-2'-hydroxyethyl ether, cholesteryl-4'-hydroxybutyl ether, 3β[N—(N'N'-dimethylaminoethyl)carbamoyl cholesterol (DC-Chol), 24(S)-hydroxycholesterol, 25-hydroxycholesterol, 25(R)-27-hydroxycholesterol, 22-oxacholesterol, 23-oxacholesterol, 24-oxacholesterol, cycloartenol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, 3,6,9-trioxaoctan-1-ol-cholesteryl-3e-ol, dehydroergosterol, 9,11-dehydroergosterol, dehydroepiandrosterone, lanosterol, dihydrolanosterol, lanostenol, lumisterol, sitocalciferol, calcipotriol, coprostanol, cholecalciferol, lupeol, ergocalciferol, 22-dihydroegocalciferol, ergosterol, brassicasterol, tomatidine, tomatine, ursolic acid, cholic acid, chenodeoxycholic acid, zymosterol, diosgenin, fucosterol, fecosterol, daucosterol, or a salt or ester thereof.

The sterol or cholesterol derivative may be conjugated to another moiety, such as an amino acid or an alkyl group.

In one embodiment, the cholesterol or derivative thereof is present at from 48 mol % to 85 mol %, 50 mol % to 85 mol %, 52 mol % to 80 mol %, 54 mol % to 80 mol %, 56 mol % to 80 mol %, 58 mol % to 80 mol %, 60 mol % to 80 mol % or 62 mol % to 80 mol % or a cholesterol or derivative thereof based on the total lipid present in the lipid nanoparticle.

In another embodiment, the cholesterol or derivative thereof is present at greater than 48 mol %, 49 mol %, 50 mol %, 51 mol %, 52 mol %, 53 mol %, 54 mol %, 55 mol %, 56 mol %, 57 mol %, 58 mol %, 59 mol %, 60 mol %, 61 mol % or 62 mol %. The upper limit of the cholesterol or cholesterol derivative content may be 88 mol %, 87 mol %, 86 mol %, 85 mol %, 84 mol %, 83 mol %, 82 mol %, 81 mol %, 80 mol %, 79 mol %, 78 mol %, 77 mol %, 76 mol % or 75 mol %. The cholesterol or cholesterol derivative content may include any combination of the foregoing lower and upper limits.

In one embodiment, the cholesterol is present at from 48 mol % to 85 mol %, 50 mol % to 85 mol %, 52 mol % to 80 mol %, 54 mol % to 80 mol %, 56 mol % to 80 mol %, 58 mol % to 80 mol %, 60 mol % to 80 mol % or 62 mol % to 80 mol % or a cholesterol based on the total lipid present in the lipid nanoparticle.

In another embodiment, the cholesterol is present at greater than 48 mol %, 49 mol %, 50 mol %, 51 mol %, 52 mol %, 53 mol %, 54 mol %, 55 mol %, 56 mol %, 57 mol %, 58 mol %, 59 mol %, 60 mol %, 61 mol % or 62 mol %. The upper limit of the cholesterol content may be 88 mol %, 87 mol %, 86 mol %, 85 mol %, 84 mol %, 83 mol %, 82 mol %, 81 mol %, 80 mol %, 79 mol %, 78 mol %, 77 mol %, 76 mol % or 75 mol %. The cholesterol content may include any combination of the foregoing lower and upper limits.

The tocopherol includes an α-tocopherol, β-tocopherol, γ-tocopherol, δ-tocopherol or a salt or ester thereof. The tocopherol may be present at 0.5 mol % to 20 mol %, 1 mol % to 15 mol % or 2 mol % to 10 mol %.

In some embodiments, the LNP comprises low levels of a cholesteryl ester comprising a fatty acid conjugated via an ester group. For example, the cholesteryl ester content may be less than 10 mol %, less than 8 mol % or less than 5 mol % or less than 2 mol %.

In another embodiment, the LNP has low levels of cationic cholesterol lipids, such as 3β-[N—(N',N'-dimethylaminoethane)-carbamoyl]cholesterol hydrochloride (DC-cholesterol). For example, the cationic cholesterol content may be less than 10 mol %, less than 8 mol %, less than 5 mol % or less than 2 mol %.

Ionizable Lipid

The LNP of the disclosure has an ionizable lipid, which includes one or a combination of two or more of such lipids. The ionizable lipid may be charged at low pH and bear substantially no net charge at physiological pH. This allows for electrostatic interactions between the lipid and the negatively charged nucleic acid cargo during initial formulation. Since the ionizable lipid is near neutral at physiological pH, toxicity and renal clearance is reduced. Without being limited by theory, after cellular uptake by endocytosis, the acidic environment of the endosome leads to an increase in the net positive charge of the ionizable amino lipids, which promotes fusion with the anionic lipids of the endosomal membrane and subsequent membrane destabilization and release of the nucleic acid-based therapeutics into the cytoplasm to exert their effects.

In some embodiments, it is desirable to include less than 50 mol % ionizable lipid in the LNP. In certain embodiments, the ionizable lipid content is from 5 mol % to 50 mol % or 8 mol % to 47 mol % or 10 mol % to 50 mol % or 15 mol % to 45 mol % or 15 mol % to 35 mol % of total lipid present in the lipid nanoparticle.

In certain embodiments, the ionizable lipid content may be less than 48 mol %, less than 45 mol %, less than 40 mol %, less than 35 mol %, less than 30 mol %, less than 25 mol %, less than 20 mol %, less than 15 mol %, less than 10 mol % or less than 5 mol %. In certain embodiments, the lower limit of the ionizable lipid content may be greater than 5 mol %, greater than 8 mol %, greater than 10 mol %, greater than 12 mol %, greater than 14 mol %, greater than 15 mol %, greater than 16 mol %, greater than 18 mol % or greater than 20 mol %. Any one of the upper limits may be combined with any one of the lower limits to arrive at a suitable ionizable lipid content in the LNP.

As used herein, the term "cationic lipid" refers to a lipid that, at a given pH, such as physiological pH, is in an electrostatically neutral form and that may either accept or donate protons, thereby becoming electrostatically positively charged, and for which the electrostatically neutral form has a calculated logarithm of the partition coefficient between water and 1-octanol (i.e., a c Log P) greater than 8. In some embodiments, the cationic lipid has a pKa that is between 5.0 and 7.0.

In some embodiments, the cationic lipid has an amino group. In some cases, the cationic lipid comprises a protonatable tertiary amine (e.g., pH titratable) head group, C16 to C18 alkyl chains, ether linkages between its head group and alkyl chains, and 0 to 3 double bonds. Such lipids include, but are not limited to sulfur lipids, such as MF019 described herein and DODMA. Other lipids that may be used in the practice of the disclosure include MC3- and KC2-type lipids, which are well-known to those of skill in the art. In further embodiments, the ionizable lipid is selected from one or more lipids set forth in WO 2022/246555; WO 2022/246568; WO 2022/24657; PCT/CA2023/050129 filed on Jan. 31, 2023; WO2022/155728; 63/340,687 filed on May 11, 2022; 63/410,281 filed on Sep. 27, 2022; 63/410,261 filed on Sep. 27, 2022; 63/434,506 filed on Dec. 22, 2022; 63/410,273 filed on Sep. 27, 2022; and 63/445,854 filed on Feb. 15, 2023, each incorporated herein by reference.

In one embodiment, the ionizable cationic lipid comprises an ionizable amino head group and at least two lipophilic groups, at least one of which comprises a heteroatom, such as an ester or one or more sulfur atoms. In some embodiments, at least one lipophilic group comprises distal branching and/or one or more cyclic groups. Examples of ionizable cationic lipids comprising an ionizable amino head group and two lipophilic chains, at least one chain comprising one or more sulfur atoms and/or ester groups are described in co-owned and co-pending 63/340,687 filed on May 11, 2022; 63/410,281 filed on Sep. 27, 2022; 63/410,261 filed on Sep. 27, 2022; 63/434,506 filed on Dec. 22, 2022; 63/410,273 filed on Sep. 27, 2022. Functional groups comprising one or more heteroatoms may be biodegradable in vivo.

In some embodiments, it is desirable to include less than 50 mol % cationic lipid in the LNP. That is, the ionizable lipid content may be less than 50 mol %, less than 45 mol %, less than 40 mol %, less than 35 mol %, less than 30 mol %, less than 25 mol %, less than 20 mol %, less than 15 mol %, less than 10 mol % or less than 5 mol %.

In certain embodiments, the cationic lipid content is from 5 mol % to 50 mol % or 8 mol % to 47 mol % or 10 mol % to 50 mol % or 15 mol % to 45 mol % or 15 mol % to 35 mol % of total lipid present in the lipid nanoparticle.

The ionizable lipid component may include an ionizable anionic lipid as part of the ionizable lipid content. An example of such a lipid is cholesteryl hemisuccinate (CHEMS). Further examples of ionizable anionic lipids are described in co-pending and co-owned U.S. provisional patent titled "Ionizable Anionic Lipids" filed on Mar. 23, 2023, which is incorporated herein by reference in its entirety.

Hydrophilic Polymer-Lipid Conjugate

In one embodiment, the lipid nanoparticle comprises a hydrophilic-polymer lipid conjugate capable of incorporation into the LNP. The conjugate includes a vesicle-forming lipid having a polar head group, and covalently attached to the head group, a polymer chain that is hydrophilic. Examples of hydrophilic polymers include polyethyleneglycol (PEG), polyvinylpyrrolidone, polyvinylmethylether, polyhydroxypropyl methacrylate, polyhydroxypropylmethacrylamide, polyhydroxyethyl acrylate, polymethacrylamide, polydimethylacrylamide, polymethyloxazoline, polyethyloxazoline, polyhydroxyethyloxazoline, polyhydroxypropyloxazoline, polysarcosine and polyaspartamide. In one embodiment, the hydrophilic-polymer lipid conjugate is a PEG-lipid conjugate. The hydrophilic polymer lipid conjugate may also be a naturally-occurring or synthesized oligosaccharide-containing molecule, such as, for example, monosialoganglioside ($G_{M1}$). The ability of a given hydrophilic-polymer lipid conjugate to enhance the circulation longevity of the LNPs herein could be readily determined by those of skill in the art using known methodologies.

The hydrophilic polymer lipid conjugate may be present in the nanoparticle at 0.5 mol % to 5 mol %, or at 0.5 mol % to 3 mol %, or at 0.5 mol % to 2.5 mol % or at 0.5 mol % to 2.0 mol % or at 0.5 mol % to 1.8 mol % of total lipid.

In another embodiment, the hydrophilic polymer-lipid conjugate is a PEG-lipid conjugate that is present in the nanoparticle at 0.5 mol % to 5 mol %, or at 0.5 mol % to 3 mol % or at 0.5 mol % to 2.5 mol % or at 0.5 mol % to 2.0 mol % or at 0.5 mol % to 1.8 mol % of total lipid.

As discussed below, the hydrophilic polymer-lipid conjugate may be conjugated to a targeting ligand at its distal end.

Low Phospholipid Content

The lipid nanoparticle has "substantially no phospholipid", meaning that the lipid nanoparticle has less than 3 mol % of a phospholipid, such as a neutral phospholipid. In one example, the lipid nanoparticle has 3 mol % or less phospholipid content. Examples of neutral phospholipids include phosphatidylcholine or phosphatidylethanolamine such as distearoylphosphatidylcholine (DSPC), distearoylphosphatidylethanolaine (DSPE), dioleoylphosphatidylethanolamine (DOPE), dioleoylphosphatidylcholine (DOPC), 1-palmitoyl-2-oleoyl-phosphatidylcholine (POPC), dipalmitoyl-phosphatidylcholine (DPPC). In some embodiments, the phospholipid is a phospholipid-sterol conjugate, such as an SPC-cholesterol, OPC-cholesterol or PPC-cholesterol conjugate. Additional, phospholipid-sterol conjugates are described in US2011/0177156, which is incorporated herein by reference.

An example of a suitable phospholipid that is an SPC-Chol conjugate is NTX-H-0001 set forth below:

In one embodiment, the lipid nanoparticle has less than 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or 0 mol % phospholipid. Most advantageously, the LNP has no phospholipid, but small amounts may not impact the LNP properties described herein.

In some examples of the disclosure, it has been found that the inclusion of small amounts of phospholipid in high sterol-containing LNPs improves liver targeting relative to Onpattro™.

In another embodiment, the lipid nanoparticle has "substantially no neutral lipid" meaning that the lipid nanoparticle has less than 3 mol % of any neutral lipid, excluding cholesterol or a cholesterol derivative. The term "neutral lipid" refers to any of a number of lipid species, including vesicle-forming lipids, that exist either in an uncharged or neutral zwitterionic form at physiological pH. In another example, the lipid nanoparticle has less than 8, 6, 4 or 2 mol % neutral lipid, such as a phospholipid and/or phospholipid conjugate.

Examples of neutral lipids include sphingomyelin, diacylphosphatidylcholines, such as distearoylphosphatidylcholine (DSPC), dioleoylphosphatidylcholine (DOPC), 1-palmitoyl-2-oleoyl-phosphatidylcholine (POPC) and dipalmitoyl-phosphatidylcholine (DPPC), diacylphosphatidylethanolamine, such as dioleoylphosphatidylethanolamine (DOPE), ceramide, cephalin, triglyceride and diacylglycerol. In some embodiments, the neutral lipid is a phospholipid-sterol conjugate, such as a SPC-cholesterol or PPC-cholesterol conjugate or those described in US2011/0177156.

An example of a suitable neutral lipid that is a SPC-Chol conjugate is NTX-H-0001 set forth above.

In one embodiment, the lipid nanoparticle has less than 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1 or 0 mol % of any neutral lipid. Most advantageously, the LNP has no neutral lipid, but small amounts may be included in the formulation without impacting the LNP properties described herein.

Additional Components

The LNP may comprise additional lipid components or modifications to the sterol (e.g., cholesterol), sterol derivative (e.g., cholesterol derivative) and/or hydrophilic polymer-lipid conjugate.

For example, the surface of the LNP may be grafted to comprise a targeting ligand. The targeting ligand may be conjugated to cholesterol, the cholesterol derivative and/or the hydrophilic polymer-lipid conjugate. The targeting ligand may be conjugated to the distal end of a hydrophilic polymer-lipid conjugate. The targeting ligand may be used

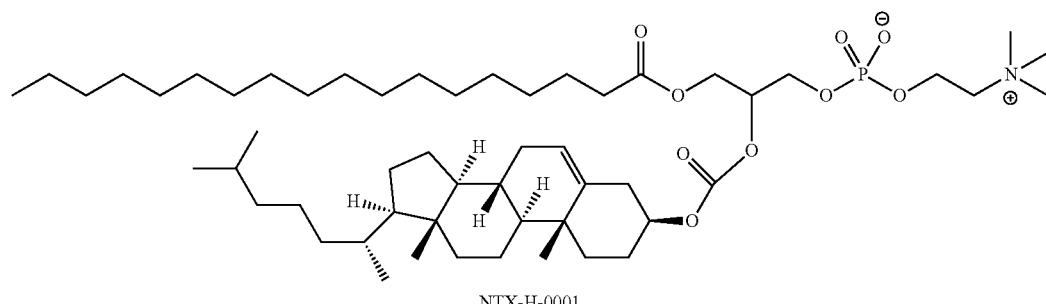

NTX-H-0001 to target receptors on cells in vivo. In some embodiments, the targeting ligand may be conjugated to any amount of phospholipid that may be included in the LNP. In such embodiments, the phospholipid-targeting ligand conjugate is typically present at less than 3 mol %.

The ligand includes peptides, polypeptides or proteins and includes antibodies or fragments thereof. In one embodiment, the ligand may be a single-chain antibody fragment.

Nanoparticle Preparation

Lipid nanoparticles can be prepared using any of a variety of suitable methods, such as a rapid mixing/ethanol dilution process. Examples of preparation methods are described in Jeffs, L. B., et al., Pharm Res, 2005, 22(3):362-72; and Leung, A. K., et al., The Journal of Physical Chemistry. C, Nanomaterials and Interfaces, 2012, 116(34): 18440-18450, each of which is incorporated herein by reference in its entirety.

For example, the method of preparing the lipid nanoparticles may comprise dissolving lipid components (e.g., ionizable lipid, a sterol, and a hydrophilic polymer-lipid) at appropriate ratios in an organic solvent (e.g., ethanol). An aqueous buffer is prepared separately at a suitable pH to ensure that the head group (e.g., amino group) of an ionizable lipid is protonated to facilitate electrostatic interaction with the negatively charged cargo, and the positively charged ionizable lipid. Such charge interaction improves encapsulation.

In some embodiments, an aqueous phase is subsequently combined with the organic solvent-lipid mixture. Combining the aqueous phase and the organic-solvent-lipid mixture may be carried out in a mixing device (e.g., in-line mixer), such as a T-junction mixer with specialized pumps (e.g., a T-tube mixer), a herringbone micromixer, a toroidal mixer, a multi-inlet vortex mixer or other suitable mixing devices known to those of skill in the art. In some embodiments, the mixing device refers to a device comprising two or more inlets meeting in a central mixing region and an outlet through which the mixture exits the device. The LNP formation may occur upon mixture of the aqueous phase and organic solvent-lipid mixture and/or subsequent to such mixing. (Kulkarni et al., 2019, Nanoscale, 11(18):9023-9031, which is incorporated herein by reference).

The aqueous phase typically comprises a buffer. Non-limiting examples of suitable buffers include MES or phosphate buffered saline (PBS). Examples of suitable solvents to prepare the organic solvent-lipid mixture are organic solvents including ethanol, isopropanol, methanol and acetone.

The aqueous phase and organic-solvent lipid mixture may be introduced to the mixer as two separate respective streams via pumps. The volumetric flow rate of each stream may be the same or different and the respective flow rates of each stream may be adjusted to achieve optimal mixing and/or LNP formation.

In some embodiments, the LNPs are prepared by solvent injection. In one embodiment, such method comprises dissolving lipids in an organic solvent and subsequent stepwise dilution of the resultant solution with an aqueous solution (e.g., buffer). This controlled step-wise dilution is achieved by mixing the aqueous and lipid streams together in a container.

The lipid nanoparticles may have an average size of between 40 and 120 nm or between 45 and 110 nm or any range therebetween. In another embodiment, the lipid nanoparticle has a PDI of less than 0.2 or less than 0.15 or less than 0.12, or less than 0.10. The nitrogen-to-phosphate ratio of the lipid nanoparticle may be 3 or 6.

The LNP generally comprises a "core" region, which may include an electron dense region and optionally an aqueous portion as visualized by cryo-TEM microscopy. Without being limiting, the electron dense region within the core may be partially surrounded by an aqueous portion within the enclosed space, entirely surrounded or enveloped by an aqueous portion within the core or may have a solid core without an aqueous portion as observed by cryo-TEM. The core may comprise nucleic acid and ionizable lipid. In one embodiment, the cholesterol, cholesterol derivative and/or tocopherol is present in an outer lipid layer and/or in the core of the LNP.

In some embodiments, the LNP is not a lipoplex. Lipoplexes are prepared by mixing preformed cationic liposomes with nucleic acid in an aqueous solution and may exhibit undesirable properties such as localization of the cargo on the particle surface. Lipoplexes lack the above-described core of the LNP particle. Further, LNPs have a defined size, shape and morphology whereas lipoplexes lack such defined physical characteristics. (See Kubota et al., 2017, Int. J. Nanomedicine, 12:5121-5133 and Kulkarni et al., 2018, Nucleic Acid Therapeutics, 28(3):146-157, which are each incorporated herein by reference).

Thus, according to some embodiments, the LNPs disclosed herein have a defined mean particle size that ranges between 40 and 120 nm or between 45 and 100 nm or between 50 and 90 nm. In some embodiments, the LNPs herein have a PDI of less than 0.20, less than 0.18, less than 0.16, less than 0.15 or less than 0.14.

As used herein, the term "encapsulation," with reference to incorporating the nucleic acid cargo within an LNP refers to any association of the nucleic acid with any lipid component or compartment of the lipid nanoparticle. However, this excludes localization of the nucleic acid on the particle surface as in lipoplexes. In some examples of the disclosure, the nucleic acid is present in the core of the LNP. Without being limited by theory, the nucleic acid may be present in micelles within the core of the LNP.

Nucleic Acid Cargo

In one embodiment, the cargo is a nucleic acid. The nucleic acid includes, without limitation, RNA, including small interfering RNA (siRNA), small nuclear RNA (snRNA), micro RNA (miRNA), messenger RNA (mRNA) or DNA such as vector DNA or linear DNA. The nucleic acid length can vary and can include nucleic acid of 1-50,000 nucleotides in length. The nucleic acid can be in any form, including single stranded DNA or RNA, double stranded DNA or RNA, or hybrids thereof. Single stranded nucleic acid includes antisense oligonucleotides. The nucleic acid may be conjugated to another molecule, including a targeting moiety. An example of such a nucleic acid conjugate is an antibody-nucleic acid conjugate, or an oligosaccharide-nucleic acid conjugate, such as a GalNAc-nucleic acid conjugate.

In one embodiment, the cargo is an mRNA, which includes a polynucleotide that encodes at least one peptide, polypeptide or protein. The mRNA includes, but is not limited to, small activating RNA (saRNA) and trans-amplifying RNA (taRNA), as described in co-pending U.S. provisional Application No. 63/195,269, titled "mRNA Delivery Using Lipid Nanoparticles", which is incorporated herein by reference.

The mRNA as used herein encompasses both modified and unmodified mRNA. In one embodiment, the mRNA comprises one or more coding and non-coding regions. The mRNA can be purified from natural sources, produced using recombinant expression systems and optionally purified, or may be chemically synthesized.

In those embodiments in which an mRNA is a chemically synthesized molecule, the mRNA can comprise nucleoside analogs such as analogs having chemically modified bases or sugars, and/or backbone modifications. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The mRNAs of the disclosure may be synthesized according to any of a variety of known methods. For example, mRNAs in certain embodiments may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor.

In some embodiments, in vitro synthesized mRNA may be purified before encapsulation to remove undesirable impurities including various enzymes and other reagents used during mRNA synthesis.

The present disclosure may be used to encapsulate mRNAs of a variety of lengths. In some embodiments, the present disclosure may be used to encapsulate in vitro synthesized mRNA ranging from about 1-20 kb, about 1-20 kb, about 1-15 kb, about 1-10 kb, about 5-20 kb, about 5-15 kb, about 5-12 kb, about 5-10 kb, about 8-20 kb, or about 8-15 kb in length.

Typically, mRNA synthesis includes the addition of a "cap" on the 5' end, and a "tail" on the 3' end. The presence of the cap is advantageous in that it may provide resistance to nucleases found in eukaryotic cells. The presence of a "tail" serves to protect the mRNA from exonuclease degradation.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 1 and 500 nucleotides in length or 50 and 500 nucleotides in length or longer.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 1 and 500 nucleotides in length or 50 and 500 nucleotides in length or longer.

While mRNA provided from in vitro transcription reactions may be desirable in certain embodiments, other sources of mRNA are contemplated, such as mRNA produced from bacteria, fungi, plants, and/or animals.

The mRNA sequence may comprise a reporter gene sequence, although the inclusion of a reporter gene sequence in pharmaceutical formulations for administration is optional. Such sequences may be incorporated into mRNA for in vitro studies or for in vivo studies in animal models to assess expression and biodistribution.

In another embodiment, the cargo is an siRNA. An siRNA becomes incorporated into endogenous cellular machineries to result in mRNA breakdown, thereby preventing transcription. Since RNA is easily degraded, its incorporation into a delivery vehicle can reduce or prevent such degradation, thereby facilitating delivery to a target site.

The siRNA encompassed by embodiments of the disclosure may be used to specifically inhibit expression of a wide variety of target polynucleotides. The siRNA molecules targeting specific polynucleotides for any therapeutic, prophylactic or diagnostic application may be readily prepared according to procedures known in the art. An siRNA target site may be selected and corresponding siRNAs may be chemically synthesized, created by in vitro transcription, or expressed from a vector or PCR product. A wide variety of different siRNA molecules may be used to target a specific gene or transcript. The siRNA may be double-stranded RNA, or a hybrid molecule comprising both RNA and DNA, e.g., one RNA strand and one DNA strand. The siRNA may be of a variety of lengths, such as 1 to 30 nucleotides in length or 15 to 30 nucleotides in length or 20 to 25 nucleotides in length. In certain embodiments, the siRNA is double-stranded and has 3' overhangs or 5' overhangs. In certain embodiments, the overhangs are UU or dTdT 3'. In particular embodiments, the siRNA comprises a stem loop structure.

In a further embodiment, the cargo molecule is a microRNA or small nuclear RNA. Micro RNAs (miRNAs) are short, noncoding RNA molecules that are transcribed from genomic DNA, but are not translated into protein. These RNA molecules are believed to play a role in regulation of gene expression by binding to regions of target mRNA. Binding of miRNA to target mRNA may downregulate gene expression, such as by inducing translational repression, deadenylation or degradation of target mRNA. Small nuclear RNA (snRNA) are typically longer noncoding RNA molecules that are involved in gene splicing. The snRNA molecules may have therapeutic or diagnostic importance in diseases that are an outcome of splicing defects.

In another embodiment, the cargo is a DNA vector. The encapsulated DNA vectors may be administered to a subject for the purpose of repairing, enhancing or blocking or reducing the expression of a cellular protein or peptide. In another embodiment, the encapsulated DNA vectors may be administered to a subject for diagnosis of disease. The DNA vector may localize in target cells (e.g., rapidly dividing cells) and expression of encoded DNA may be used to provide a measurable signal. Accordingly, the nucleotide polymers can be nucleotide sequences including genomic DNA, cDNA, or RNA.

As will be appreciated by those of skill in the art, the vectors may encode promoter regions, operator regions or structural regions. The DNA vectors may contain double-stranded DNA or may be composed of a DNA-RNA hybrid. Non-limiting examples of double-stranded DNA include structural genes, genes including operator control and termination regions, and self-replicating systems such as vector DNA.

Single-stranded nucleic acids include antisense oligonucleotides (complementary to DNA and RNA), ribozymes and triplex-forming oligonucleotides. In order to have prolonged activity, the single-stranded nucleic acids will most advantageously have some or all of the nucleotide linkages substituted with stable, non-phosphodiester linkages, including, for example, phosphorothioate, phosphorodithioate, phophoroselenate, or O-alkyl phosphotriester linkages.

The DNA vectors may include nucleic acids in which modifications have been made in one or more sugar moieties and/or in one or more of the pyrimidine or purine bases. Such sugar modifications may include replacement of one or more hydroxyl groups with halogens, alkyl groups, amines, azido groups or functionalized as ethers or esters. In another embodiment, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

The DNA vector may be modified in certain embodiments with a modifier molecule such as a peptide, protein, steroid or sugar moiety. Modification of a DNA vector with such molecule may facilitate delivery to a target site of interest. In some embodiments, such modification translocates the DNA vector across a nucleus of a target cell. By way of example, a modifier may be able to bind to a specific part of the DNA vector (typically not encoding of the gene-of-interest), but also has a peptide or other modifier that has nucleus-homing effects, such as a nuclear localization signal. A non-limiting example of a modifier is a steroid-peptide nucleic acid conjugate as described by Rebuffat et al., 2002, Faseb J. 16(11):1426-8, which is incorporated herein by reference. The DNA vector may contain sequences encoding different proteins or peptides. Promoter, enhancer, stress or chemically-regulated promoters, antibiotic-sensitive or nutrient-sensitive regions, as well as therapeutic protein encoding sequences, may be included as required. Non-encoding sequences may be present as well in the DNA vector.

The nucleic acids used in the present disclosure can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Known procedures for solid phase synthesis of nucleic acids by phosphite-triester, phosphotriester, and H-phosphonate chemistries are widely available.

In one embodiment, the DNA vector is double stranded DNA and comprises more than 700 base pairs, more than 800 base pairs or more than 900 base pairs or more than 1000 base pairs.

Improvements in Liver-Specific Expression

In some embodiments, the LNP exhibits "liver-specific expression" of the protein or peptide encoded by the cargo nucleic acid, meaning that the cargo nucleic acid has increased expression of the protein or peptide in the liver over the spleen by at least 10-fold, at least 20-fold, at least 30-fold, at least 40-fold, at least 50-fold or at least 60-fold. In some embodiments, the cargo nucleic acid is mRNA or vector DNA. In one example, the nucleic acid is mRNA.

In some embodiments, the inclusion of a small amount of neutral lipid may improve the liver-specific expression of LNPs having elevated levels of sterol or a sterol derivative relative to Onpattro™. For example, the neutral lipid content may be between 0 and 10 mol % or 0.5 to 10 mol % or 1 mol % to 8 mol % or 1 mol % to 5 mol % or 1 mol % to 3.5 mol % to improve liver targeting.

In further embodiments, the inclusion of low levels of a hydrophilic-polymer lipid conjugate may improve liver-specific expression of LNPs having elevated levels of sterol or a sterol derivative relative to Onpattro™. For example, the hydrophilic-polymer lipid conjugate content to achieve such improved liver targeting may be less than 2.5 mol %, less than 2.25 mol %, less than 2.0 mol %, less than 1.75 mol %, less than 1.5 mol % or less than 1.25 mol %.

Alternatively or additionally, the increased expression of the protein or peptide encoded by the nucleic acid cargo (e.g., mRNA or vector DNA) in the liver over the spleen is at least 5% or 10% greater than the increased expression in an Onpattro™ LNP in the liver over the spleen measured under otherwise identical conditions and encapsulating the same cargo.

The examples are intended to illustrate the preparation of specific lipid nanoparticle preparations and properties thereof but are in no way intended to limit the scope of the invention.

The article "a" or "an" as used herein is meant to include both singular and plural, unless otherwise indicated.

EXAMPLES

Example 1: LNPs Containing Elevated Cholesterol Levels have High Encapsulation Efficiency This example examines the effect of increasing cholesterol content and decreasing ionizable lipid content on the physical properties of lipid nanoparticles lacking phospholipid.

Phospholipid-free LNPs or LNPs having substantially no phospholipid having various concentrations of cholesterol were prepared by injecting volumes of lipid mixture (ionizable lipid (DLin-MC3-DMA, herein "MC3")), cholesterol, PEG-DMG) at respective mol % ratios of X/98.5-X/1.5 from a range of 15-45 mol % ionizable lipid dissolved in ethanol to a final concentration of 10 mM with an aqueous phase containing nucleic acid cargo through a T-junction at a 3:1 aqueous:ethanol (v/v) ratio and an amine-to-phosphate (N/P) ratio of 6. Flow rates were set to 5 mL/min for the lipid phase and 15 mL/min for the aqueous phase containing mRNA dissolved in 25 mM sodium acetate (pH 4) culminating in an output flow rate of 20 mL/min. The resulting formulation was then dialyzed against a 1000-fold volume of phosphate-buffered saline (pH 7.4) over a period of 24 hours in order to remove ethanol from the formulation. The nucleic acid cargo was anti-sense oligonucleotide targeting c-myc or siRNA targeted towards the firefly luciferase gene (siLuc).

FIG. 1 shows the effect of increasing the mol % of cholesterol in phospholipid-free LNPs (containing ionizable lipid, cholesterol, PEG-DMG) encapsulating anti-sense oligonucleotide at respective mol % ratios of X/98.5-X/1.5 (ionizable lipid/chol/PEG-DMG).

Surprisingly, the phospholipid-free LNPs having the highest percentage encapsulation of cargo (anti-sense oligonucleotide) contained the highest levels of cholesterol examined in the data set, namely 53.5 mol %, 58.5 mol % and 63.5 mol %. Notably, each of these formulations had an encapsulation efficiency that approached 100%. These LNPs also exhibited favourable PDI values (less than 0.1) and a suitable particle size (about 60 nm).

Figure 2A:
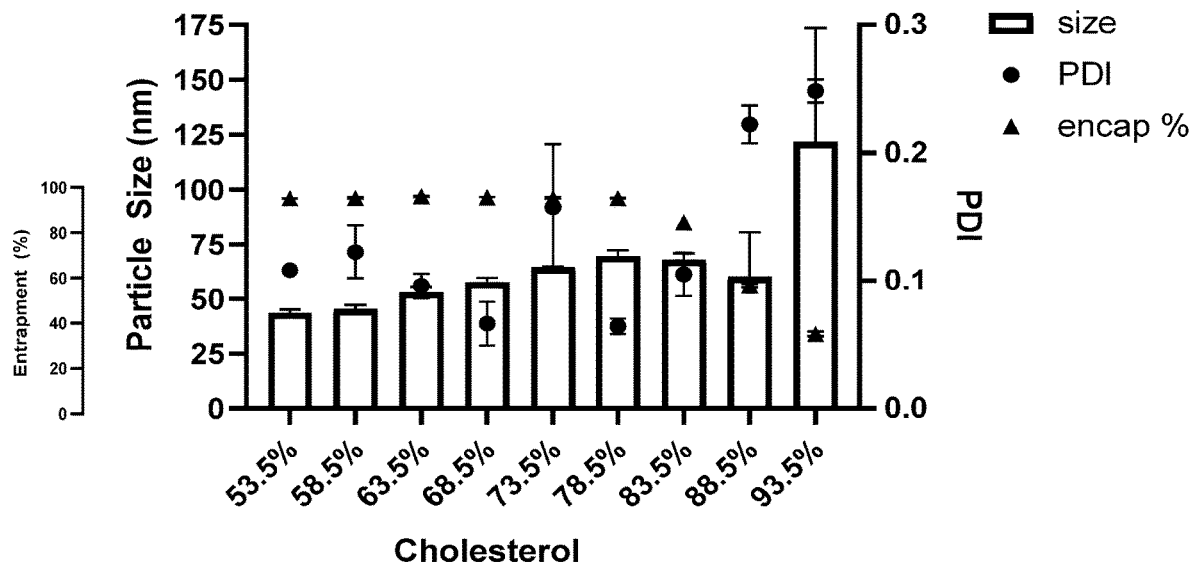
FIG. 2A is a graph showing entrapment (%), particle size (nm) and PDI of LNPs (MC3 ionizable lipid/cholesterol/PEG-DMG) at respective mol % ratios of X/98.5-X/1.5 encapsulating firefly luciferase gene (siLuc) siRNA as a function of increasing cholesterol content. The cholesterol content was increased from 53.5 mol % to 93.5 mol %. The nitrogen-to-phosphate (N/P) ratio was 6.

FIG. 2A illustrates the effect of increasing the cholesterol content on the physical properties of phospholipid-free LNPs beyond what was examined in FIG. 1, namely from 53.5 mol % to 93.5 mol %. Surprisingly, when the cholesterol content of the phospholipid-free LNPs was within the range of 53.5 mol % to 83.5 mol %, the encapsulation efficiency of the cargo (siLuc) approached 100%. The LNP size and PDI were also acceptable within this cholesterol mol % range. Above 83.5 mol % cholesterol, the LNPs exhibited high PDI values (greater than 0.2) and the LNP particle size was greater than 100 nm.

Figure 2B:
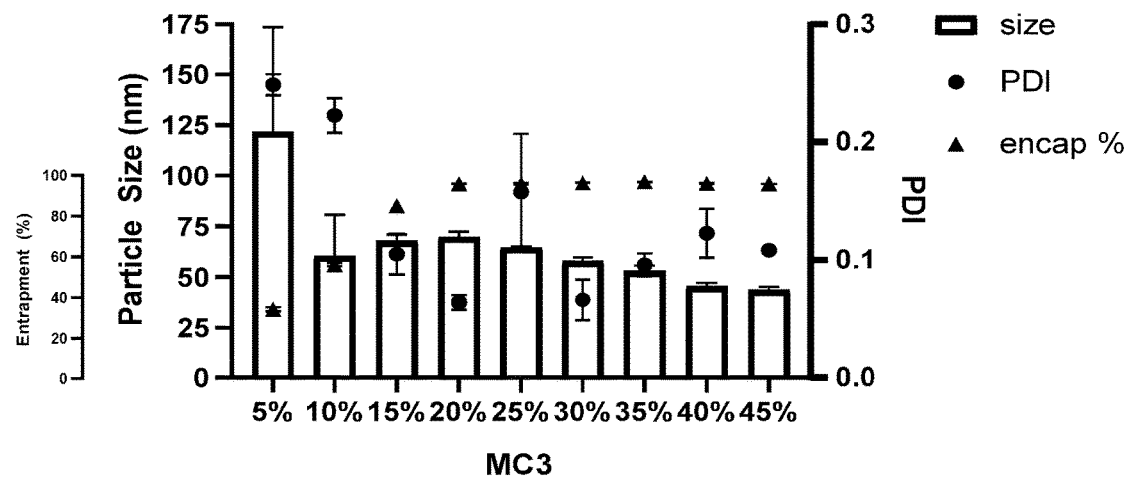
FIG. 2B is a graph showing entrapment (%), particle size (nm) and PDI of lipid nanoparticles (MC3 ionizable cationic lipid/cholesterol/PEG-DMG) at respective mol % ratios of X/98.5-X/1.5 encapsulating siLuc-siRNA as a function of increasing MC3 ionizable cationic lipid content. The ionizable cationic lipid content was increased from 5 mol % to 45 mol %. The nitrogen-to-phosphate (N/P) ratio was 6.

FIG. 2B is a plot of the physical characterization data in FIG. 2A but depicted as a function of ionizable lipid (MC3) content (instead of cholesterol content). As discussed, the benchmark Onpattro™ formulation has high levels of ionizable lipid (50 mol %), with the remainder of the lipid components being DSPC (10 mol %), cholesterol (38.2 mol %) and PEG-DMG (1.5 mol %). However, quite surprisingly, in the phospholipid-free LNPs investigated here, MC3 contents as low as 15 mol % exhibited encapsulation efficiencies approaching 100%, as well as PDI values below 0.2 and particle sizes in the range of 50 nm to 75 nm. The data also shows that LNPs having an MC3 mol % between 20% and 45 mol % showed a consistent level of encapsulation of about 100%.

Example 2: Phospholipid-Free, Luciferase mRNA-LNPs Containing Elevated Cholesterol Levels and Reduced Levels of MC3 have Comparable In Vitro Potency to the Onpattro™ Formulation This example demonstrates that MC3/cholesterol/PEG-DMG (35/63.5/1.5 mol:mol) LNPs encapsulating luciferase mRNA have comparable in vitro potency to the Onpattro™ formulation in an assay measuring luminescence verses dose of mRNA in tissue culture.

The MC3/cholesterol/PEG-DMG (35/63.5/1.5 mol:mol) and Onpattro™ (MC3/distearoylphosphatidylcholine (DSPC)/cholesterol/PEG-DMG 50/10/38.5/1.5) LNPs encapsulating the mRNA were prepared by injecting volumes of lipid mixture (ionizable lipid, cholesterol, PEG-DMG) at respective mol % ratios dissolved in ethanol to a final concentration of 10 mM with an aqueous phase containing the mRNA encoding luciferase through a T-junction at a 3:1 aqueous:ethanol (v/v) ratio and an amine-to-phosphate (N/P) ratio of 6. Flow rates were set to 5 mL/min for the lipid phase and 15 mL/min for the aqueous phase containing mRNA dissolved in 25 mM sodium acetate (pH 4) culminating in an output flow rate of 20 mL/min. The resulting formulation was then dialyzed against 1000-fold volume of phosphate-buffered saline (pH 7.4) over a period of 24 hours in order to remove ethanol from the formulation.

Huh7 cells were seeded in clear, flat bottom 96 well plates at 8,000 cells per well after reaching approximately 80% confluency. After 24 hours of growth, the initial media was exchanged for media containing the LNPs encapsulating luciferase mRNA at a dose titration of 0.03 µg/mL-10 µg/mL. Each cell treatment was performed in triplicate. After 24 hours, the media was aspirated and 100 µL of Glo Lysis Buffer™ (Promega™) was added to each well. Each plate was then subjected to incubation for 10 at 37° C. before 50 µL from each well was transferred into a white, flat bottom 96 well plate for luminescence measurements. 50 µL of Steady-Glo Luciferase™ substrate was then added into each well before luminescence readings were immediately measured through a BioTek Synergy Neo2 Hybrid Multi-Mode Reader™.

Figure 3:
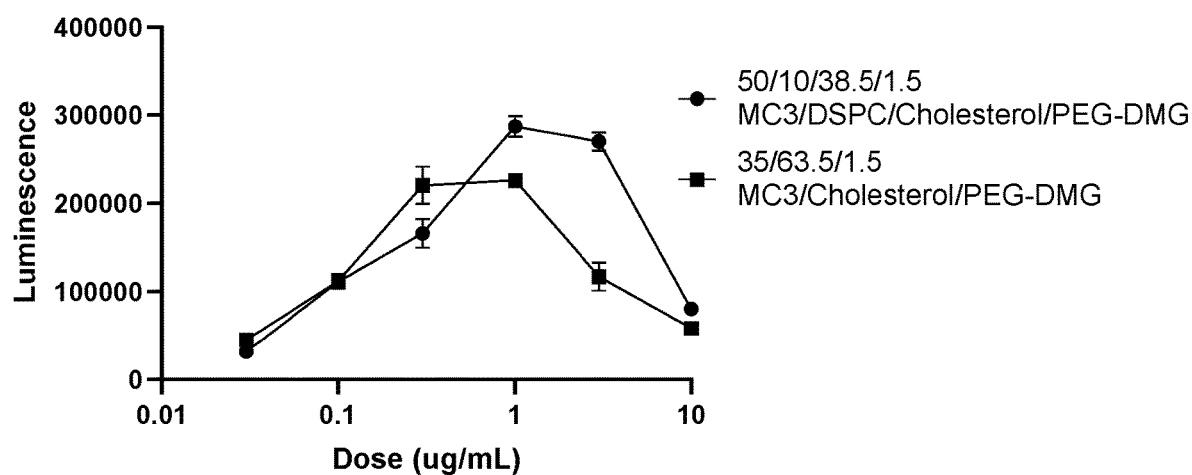
FIG. 3 is a graph showing in vitro luminescence as a function of mRNA dose for Huh7 cells after treatment with MC3 ionizable cationic lipid/cholesterol/PEG-DMG LNP at molar ratios of 35/63.5/1.5 verses an Onpattro™ LNP formulation (50/10/38.5/1.5 of MC3/DSPC/cholesterol/PEG-DMG; mol/mol) encapsulating luciferase mRNA. The nitrogen-to-phosphate (N/P) ratio was 6.

The results shown in FIG. 3 illustrate that luminescence intensity of luciferase expressed from the mRNA was comparable over the dose range of the Luc-mRNA LNPs between MC3/cholesterol/PEG-DMG (35/63.5/1.5 mol:mol) and the Onpattro™ formulation. This is surprising in part because the MC3/cholesterol/PEG-DMG formulation has 15 mol % less of the MC3 ionizable lipid than the Onpattro™ formulation and lacks phospholipid.

Example 3: Phospholipid-Free, Luciferase mRNA-LNPs Containing Elevated Cholesterol Levels and Reduced Levels of MC3 have Comparable In Vivo Potency to the Onpattro™ Formulation This example demonstrates that a variety of different LNPs having elevated cholesterol content and reduced ionizable lipid content relative to Onpattro™ and encapsulating luciferase mRNA have comparable in vivo potency to the Onpattro™ formulation.

The phospholipid-free, MC3/cholesterol/PEG-DMG (X/98.5-X/1.5 molar ionizable lipid/chol/PEG-DMG)) and Onpattro™ formulations (MC3/Chol/DSPC/PEG-DMG at 50/38.5/10/1.5) encapsulating Luc-mRNA were prepared as described in Example 2.

Figure 4A:
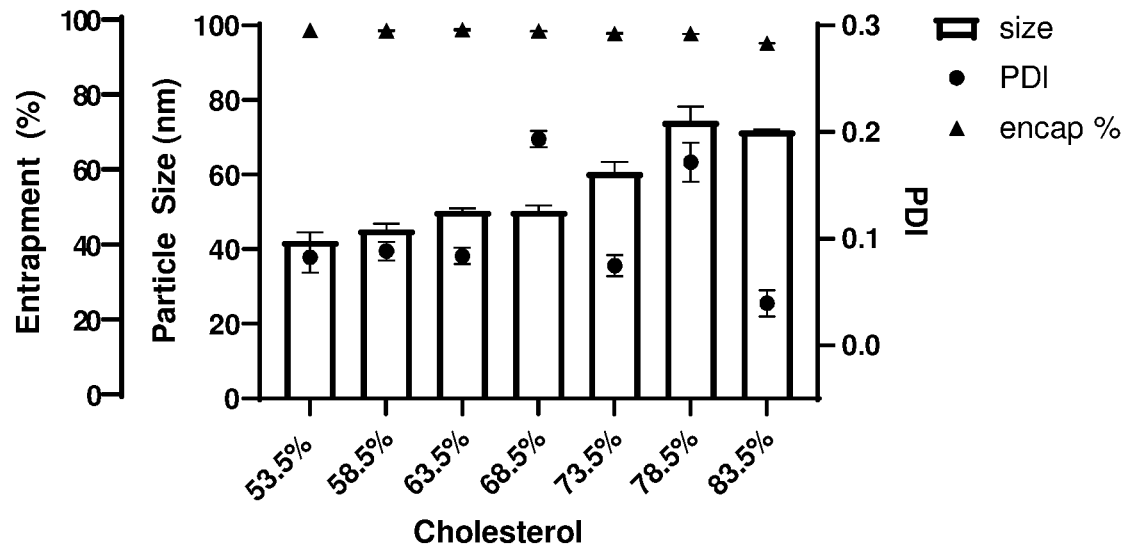
FIG. 4A is a graph showing entrapment (%), particle size (nm) and PDI of LNPs (MC3 ionizable cationic lipid/cholesterol/PEG-DMG) at respective mol % ratios of X/98.5-X/1.5 encapsulating firefly luciferase mRNA as a function of increasing cholesterol content. The cholesterol content was increased from 53.5 mol % to 83.5 mol %. The nitrogen-to-phosphate (N/P) ratio was 6.
Figure 4B:
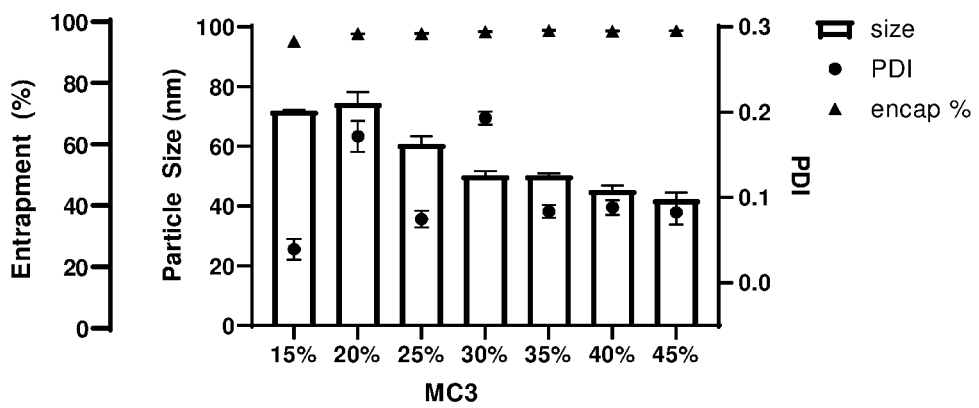
FIG. 4B is a graph showing entrapment (%), particle size (nm) and PDI of lipid nanoparticles (MC3 ionizable cationic lipid/cholesterol/PEG-DMG) at respective mol % ratios of X/98.5-X/1.5 encapsulating firefly luciferase mRNA as a function of increasing MC3 ionizable cationic lipid content. The ionizable cationic lipid content was increased from 15 mol % to 45 mol %. The nitrogen-to-phosphate (N/P) ratio was 6.

FIGS. 4A and 4B show biophysical data for the formulations tested. Similar to the formulations tested in Example 2, the encapsulation efficiency for the formulations having 53.5-83.5 mol % cholesterol approached 100% for each LNP (FIG. 4A) despite having correspondingly decreasing levels of MC3 ionizable lipid (45 mol % to 15 mol %; see FIG. 4B). The PDI and size were acceptable for each formulation tested.

For the in vivo studies, the final dose of mRNA in the formulations was 1 mg/kg of mRNA. The Luc-mRNA formulations were administered to CD-1 mice and 4 hours post-injection the liver and spleen were extracted. The mRNA luminescence was measured by Promega™ Steady-Glo™ Luciferase Assay System.

Figure 5A:
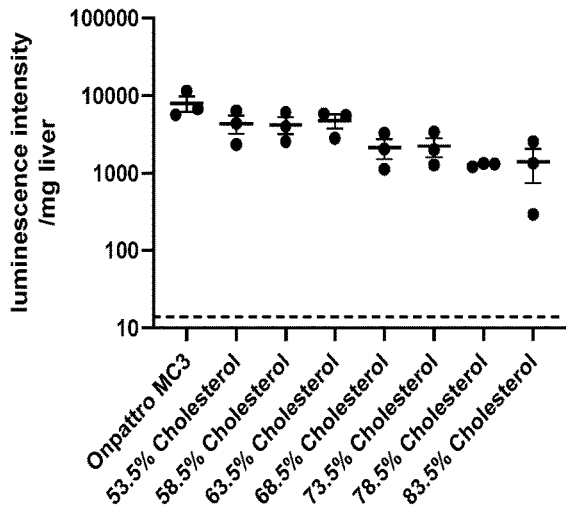
FIG. 5A is a graph showing in vivo luminescence of luciferase mRNA following liver extraction of CD-1 mice after treatment with LNPs (MC3 ionizable cationic lipid/cholesterol/PEG-DMG) at respective mol % ratios of X/98.5-X/1.5 encapsulating firefly luciferase mRNA as a function of increasing cholesterol content verses an Onpattro™ formulation (50/10/38.5/1.5 of MC3/DSPC/cholesterol/PEG-DMG; mol/mol) encapsulating luciferase mRNA. The nitrogen-to-phosphate (N/P) ratio was 6.
Figure 5B:
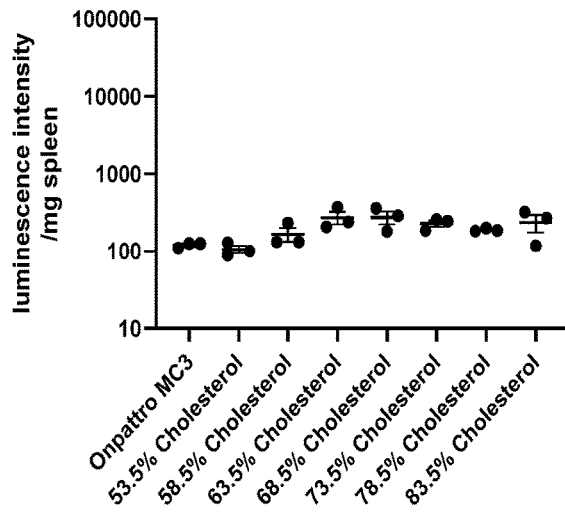
FIG. 5B is a graph showing in vivo luminescence of luciferase mRNA following extraction of the spleen of CD-1 mice after treatment with luciferase mRNA-containing LNPs (MC3 ionizable cationic lipid/cholesterol/PEG-DMG) at respective mol % ratios of X/98.5-X/1.5 as a function of increasing cholesterol content verses a luciferase mRNA-containing Onpattro™ formulation (50/10/38.5/1.5 of MC3/DSPC/cholesterol/PEG-DMG; mol/mol). The nitrogen-to-phosphate (N/P) ratio was 6.
Figure 5C:
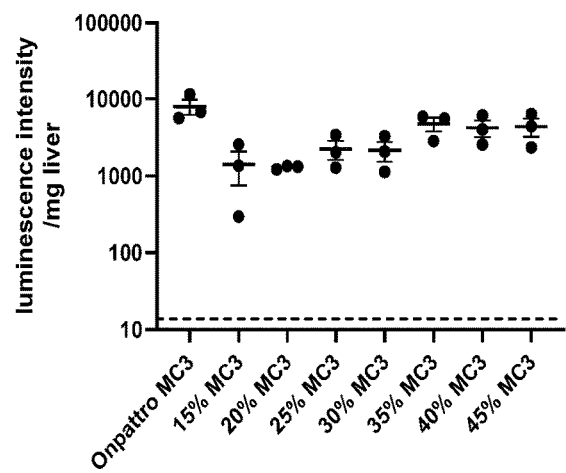
FIG. 5C is a graph showing in vivo luminescence of luciferase mRNA following liver extraction of CD-1 mice after treatment with luciferase mRNA-containing LNPs (MC3 ionizable cationic lipid/cholesterol/PEG-DMG) at respective mol % ratios of X/98.5-X/1.5 as a function of increasing MC3 lipid content verses a luciferase mRNA-containing Onpattro™ formulation (50/10/38.5/1.5 of MC3/DSPC/cholesterol/PEG-DMG; mol/mol). The nitrogen-to-phosphate (N/P) ratio was 6.
Figure 5D:
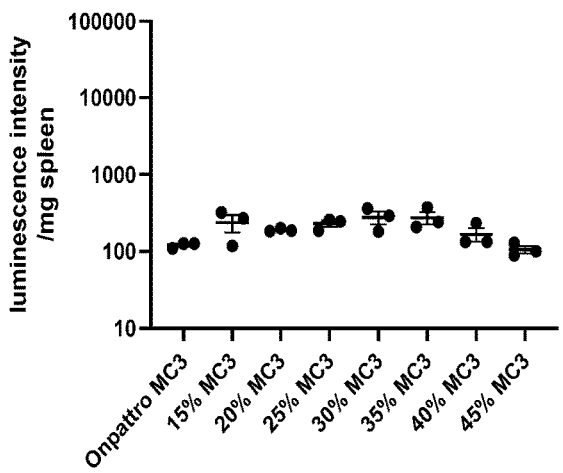
FIG. 5D is a graph showing in vivo luminescence of luciferase mRNA following spleen extraction of CD-1 mice after treatment with luciferase mRNA-containing LNPs (MC3 ionizable cationic lipid/cholesterol/PEG-DMG) at respective mol % ratios of X/98.5-X/1.5 as a function of increasing MC3 content versus a luciferase mRNA-containing Onpattro™ formulation (50/10/38.5/1.5 of MC3/DSPC/cholesterol/PEG-DMG; mol/mol). The nitrogen-to-phosphate (N/P) ratio was 6.

FIG. 5A-D shows that the luminescence in the liver and spleen for each formulation examined. FIG. 5A and FIG. 5B show the luminescence intensity/mg tissue as a function of increasing cholesterol content for the liver and spleen respectively. As the cholesterol was increased from 53.5 mol % to 83.5 mol %, the luminescence intensity/mg liver was similar for each formulation tested. In addition, the luminescence intensities for the formulations having increasing cholesterol content were similar to that of the Onpattro™ formulation. FIG. 5C and FIG. 5D show the same data plotted as a function of increasing ionizable cationic lipid content and likewise show similar luminescence intensity for formulations having different ionizable cationic lipid content. Notably, formulations having an ionizable cationic lipid content as low as 15 mol % ionizable cationic lipid and a cholesterol content of 83.5 mol % exhibited luminescence intensity in the liver and spleen generally comparable to Onpattro™. This is surprising in part because this latter MC3/cholesterol/PEG-DMG formulation had 35 mol % less of the MC3 ionizable cationic lipid than the Onpattro™ formulation and lacks phospholipid. Furthermore, in each case, the LNPs exhibited higher expression of mRNA luciferase in the liver relative to the spleen.

Example 4: Increasing the PEG-Lipid Content Above 3 Mol % Decreases Luminescence Intensity In Vivo The effect of increasing the PEG-lipid content above 1.5 mol % on luminescence intensity for Luc mRNA-containing LNPs in the liver and spleen was next explored. The LNPs examined contained MC3/cholesterol/PEG-DMG at 35/63.5/1.5 mol % and 35/61.7/3.3 mol % and were prepared as set forth in Example 2. The in vivo studies to assess mRNA luminescence intensity were conducted using as described previously in Example 3.

Figure 6A:
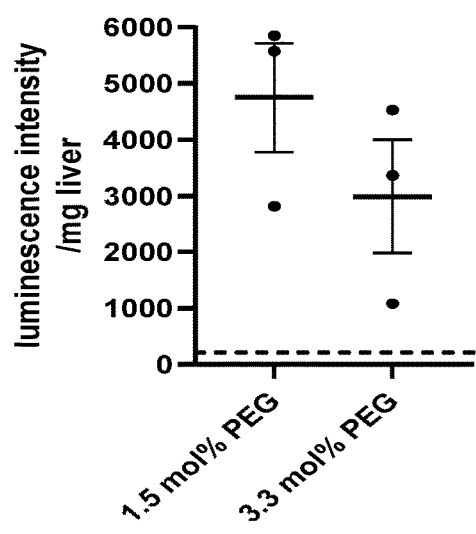
FIG. 6A is a graph showing in vivo luminescence of luciferase mRNA following liver extraction of CD-1 mice after treatment with mRNA luciferase-containing LNPs with MC3 ionizable cationic lipid/cholesterol/PEG-DMG) at respective ratios of 35/63.5/1.5 mol % and 35/61.7/3.3 mol %.
Figure 6B:
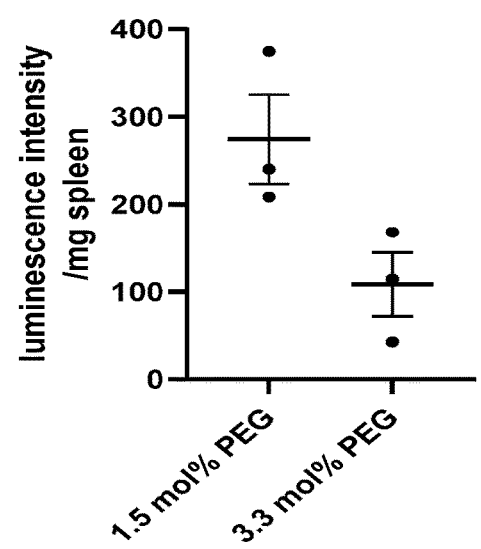
FIG. 6B is a graph showing in vivo luminescence of luciferase mRNA following extraction of spleen from CD-1 mice after treatment with mRNA luciferase-containing LNPs with MC3 ionizable cationic lipid/cholesterol/PEG-DMG) at respective ratios of 35/63.5/1.5 mol % and 35/61.7/3.3 mol %.

FIG. 6A shows that in the liver, the luminescence intensity was almost two-fold higher for the LNPs containing 1.5 mol % PEG-lipid than the LNPs containing 3.3 mol % PEG-lipid. FIG. 6B shows that in the spleen, the luminescence intensity was almost three times higher for the LNPs containing 1.5 mol % PEG-lipid than the LNPs containing 3.3 mol % PEG-lipid.

These results show that the PEG-lipid content in some embodiments is most advantageously less than 3 mol %.

conducted using the procedure as described previously in Example 3. The liver and spleen were excised and assessed for mRNA expression (luminescence intensity) at 4 hours post-injection as described above.

The inventors first examined the in vivo expression of mRNA with varying levels of DSPC and a SPC-cholesterol conjugate in which one acyl chain of DSPC is substituted with cholesterol (see structure of H-0001 above). In particular, the high cholesterol LNP formulations examined included a three-component LNP having MC3, cholesterol at 56.5 mol % and PEG-DMG at 1.5 mol % and two four-component high cholesterol LNPs with 3 mol % DSPC or SPC-chol conjugate included in the formulation at the expense of cholesterol.

TABLE 1

High sterol mRNA-LNP formulations prepared to examine liver vs spleen mRNA expression in vivo with or without phospholipid

| Sample | LNP composition | Molar ratios | Cholesterol (mol %) | Phospholipid or lyso-chol conjugate |
|---|---|---|---|---|
| A | Onpattro ™ (MC3/Chol/DSPC/PEG-DMG) | 50/38.5/10/1.5 | 38.5 | 10 |
| B | MC3/Chol/PEG-DMG | 42/56.5/1.5 | 56.5 | 0 |
| C | MC3/DSPC/Chol/PEG-DMG | 42/3/53.5/1.5 | 53.5 | 3 |
| D | MC3/SPC-Chol* (H-001)/Chol/PEG-DMG | 42/3/53.5/1.5 | 53.5 | 3 |

*SPC-Chol is a conjugate in which one acyl chain of DSPC is replaced with cholesterol referred to as "H-0001" (see above).

Furthermore, for each formulation examined, the LNPs exhibited higher expression of mRNA luciferase in the liver relative to the spleen (see FIG. 6A vs. 6B). FIG. 6A shows that in the liver, the luminescence intensity was almost two-fold higher for the LNPs containing 1.5 mol % PEG-lipid than the LNPs containing 3.3 mol % PEG-lipid. FIG. 6B shows that in the spleen, the luminescence intensity was almost three times higher for the LNPs containing 1.5 mol % PEG-lipid than the LNPs containing 3.3 mol % PEG-lipid. These results show that the PEG-lipid content in some embodiments is mostly advantageously less than 3 mol %. Furthermore, for each formulation examined, the LNPs exhibited higher expression of mRNA luciferase in the liver relative to the spleen (see FIG. 6A vs. 6B).

Example 5: High Sterol LNP Formulations are Targeted to the Liver Over the Spleen As noted, Examples 3 and 4 above suggest that high sterol mRNA LNPs result in increased levels of mRNA expression in vivo in the liver relative to the spleen (see FIGS. 5A-D and FIGS. 6A and 6B). Comparing FIGS. 5A and 5B, the luminescence intensity/mg liver (FIG. 5A) was higher for each high cholesterol LNP formulation (53.5 mol % to 83.5% cholesterol) by as much as 1,000-fold relative to the luminescence intensity/mg spleen for the same formulations (FIG. 5B). A similar trend of liver targeting was observed with LNP formulations containing ionizable cationic lipid/cholesterol/PEG-DMG at respective ratios of 35/63.5/1.5 mol % and 35/61.7/3.3 mol % (FIG. 6A vs. 6B).

Figure 7A:
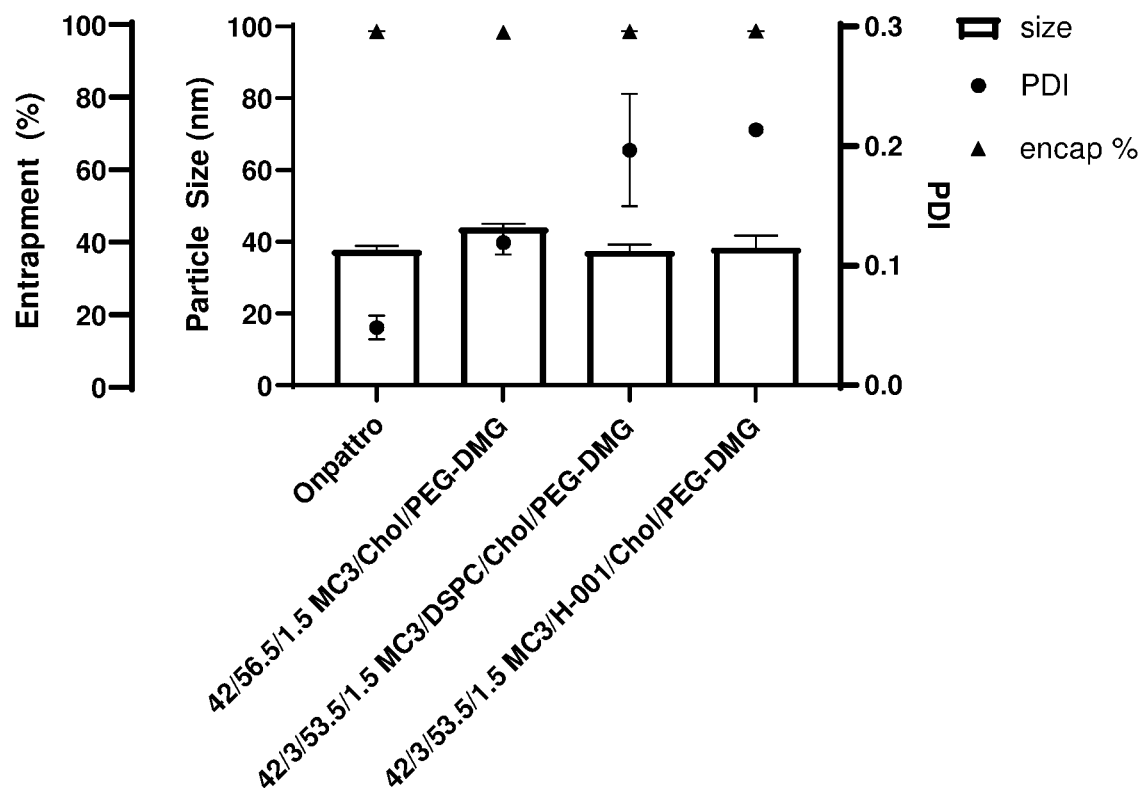
FIG. 7A is a graph showing entrapment (%), particle size (nm) and PDI of Onpattro™ (MC3/Chol/DSPC/PEG-DMG; 50/38.5/10/1.5 mol %), MC3/Chol/PEG-DMG (42/56.5/1.5 mol %), MC3/DSPC/Chol/PEG-DMG (42/3/53.5/1.5 mol %) and MC3/SPC-Chol (H-001)/Chol/PEG-DMG (42/3/53.5/1.5 mol %). The lipid nanoparticles encapsulate mRNA encoding luciferase and the N/P is 6.

In this example, and those that follow, the impact of varying the lipid components in high sterol LNPs to enhance mRNA expression in the liver relative to the spleen was examined in more detail. The LNPs were prepared as described in Example 2 above and in vivo studies to assess mRNA luminescence intensity in the liver and spleen were The formulation characteristics including size (nm), PDI and encapsulation percent for each LNP were assessed as described in Example 1 and the results are presented in FIG. 7A.

Figure 7C:
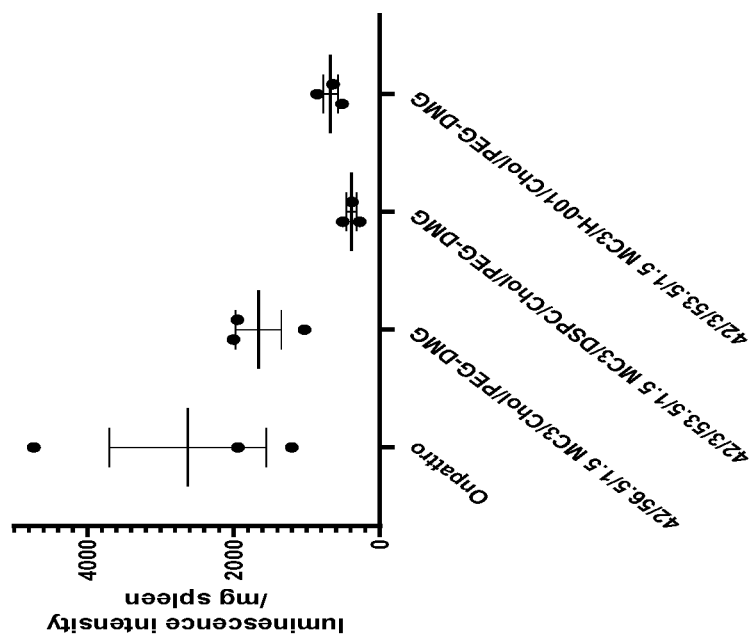
FIG. 7C is a graph showing in vivo luminescence of luciferase mRNA following extraction of spleen from CD-1 mice after treatment with mRNA luciferase-containing LNPs Onpattro™ (MC3/Chol/DSPC/PEG-DMG; 50/38.5/10/1.5 mol %), MC3/Chol/PEG-DMG (42/56.5/1.5 mol %), MC3/DSPC/Chol/PEG-DMG (42/3/53.5/1.5 mol %) and MC3/SPC-Chol (H-001)/Chol/PEG-DMG (42/3/53.5/1.5 mol %).
Figure 7B:
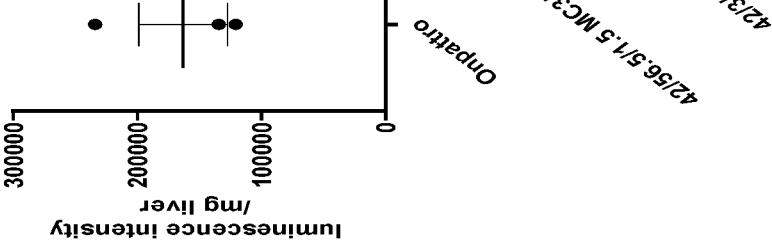
FIG. 7B is a graph showing in vivo luminescence of luciferase mRNA following liver extraction of CD-1 mice after treatment with mRNA luciferase-containing LNPs Onpattro™ (MC3/Chol/DSPC/PEG-DMG; 50/38.5/10/1.5 mol %), MC3/Chol/PEG-DMG (42/56.5/1.5 mol %), MC3/DSPC/Chol/PEG-DMG (42/3/53.5/1.5 mol %) and MC3/SPC-Chol (H-001)/Chol/PEG-DMG (42/3/53.5/1.5 mol %).

The high sterol formulations (Samples B-D) have comparable mRNA expression as Onpattro™ (Sample A) but surprisingly are more liver-tropic in that lower mRNA expression levels were observed in the spleen relative to the liver with the inventive formulations compared to Onpattro™ (see FIG. 7B vs FIG. 7C). Notably, with the inclusion of 3 mol % phospholipid (DSPC and SPC-Chol conjugate) in the high sterol LNPs, there is a further decrease in splenic activity (Samples C and D above) relative to the Sample B lacking phospholipid.

Example 6: Increasing N/P in High Sterol Formulations does not Impact Liver Activity but Maintains Liver Tropism To determine the impact of varying the amine-to-phosphate ratio (N/P) on liver targeting, a high sterol mRNA-LNP formulation of MC3/SPC-Chol conjugate/Chol/PEG-DMG at 42/3/53.5/1.5 mol % (Formulation D in Table 1) was prepared at N/P values of 5, 6, 7, 8 and 9. The LNPs were prepared as described in Example 2 above and in vivo studies to assess mRNA luminescence intensity in the liver and spleen were conducted using the procedure as described previously in Example 3.

Figure 8A:
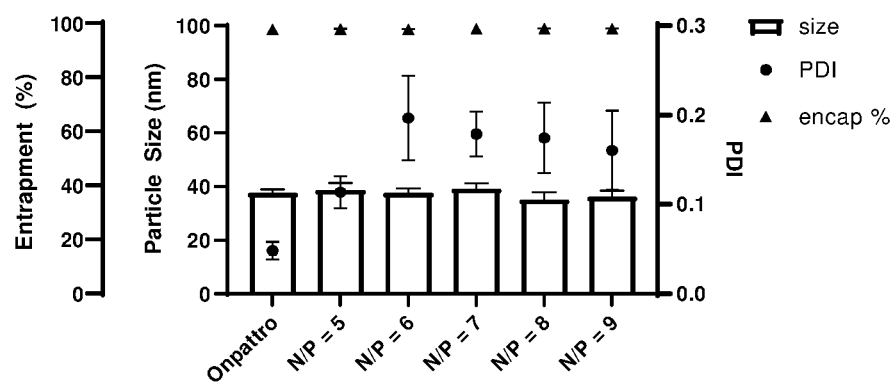
FIG. 8A is a graph showing entrapment (%), particle size (nm) and PDI of Onpattro™ (MC3/Chol/DSPC/PEG-DMG; 50/38.5/10/1.5 mol %) and a formulation of MC3/SPC-Chol conjugate/Chol/PEG-DMG at 42/3/53.5/1.5 mol % at N/P of 5, 6, 7, 8 and 9. The lipid nanoparticles encapsulate mRNA encoding luciferase. The N/P of the Onpattro™ formulation was 6.

The formulation characteristics including size (nm), PDI and encapsulation percent of mRNA encoding luciferase for each LNP were assessed as described in Example 1 and the results are presented in FIG. 8A.

Figure 8C:
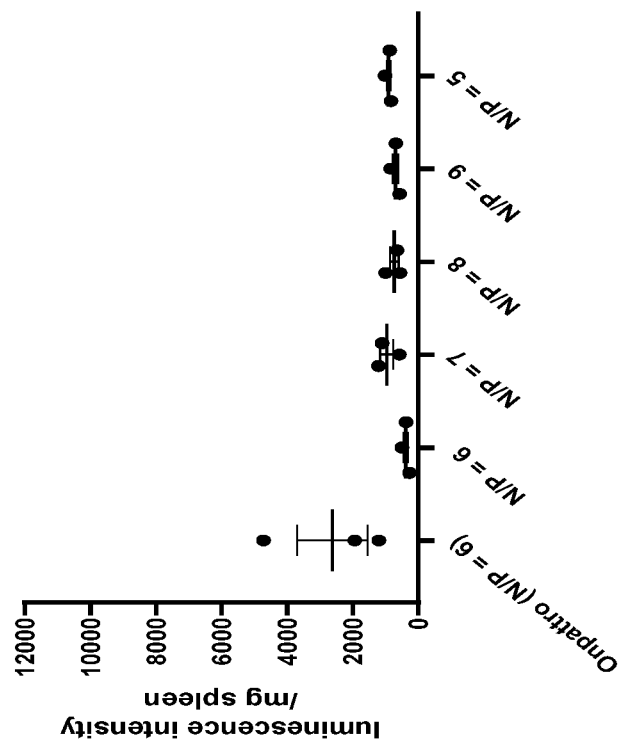
FIG. 8C is a graph showing in vivo luminescence of luciferase mRNA following extraction of spleen from CD-1 mice after treatment with mRNA luciferase-containing LNPs Onpattro™ (MC3/Chol/DSPC/PEG-DMG; 50/38.5/10/1.5 mol %) and a formulation of MC3/SPC-Chol conjugate/Chol/PEG-DMG at 42/3/53.5/1.5 mol % at N/P of 5, 6, 7, 8 and 9. The lipid nanoparticles encapsulate mRNA encoding luciferase. The N/P of the Onpattro™ formulation was 6.
Figure 8B:
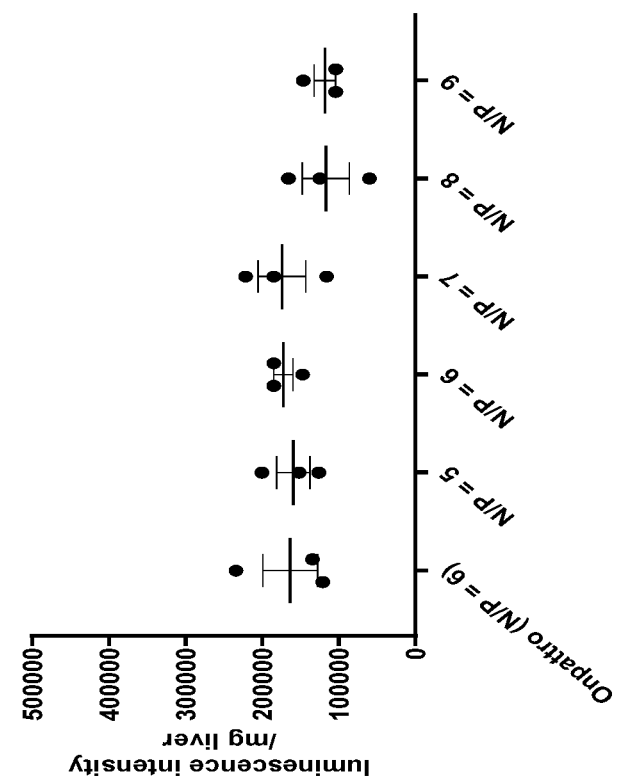
FIG. 8B is a graph showing in vivo luminescence of luciferase mRNA following liver extraction of CD-1 mice after treatment with mRNA luciferase-containing LNPs Onpattro™ (MC3/Chol/DSPC/PEG-DMG; 50/38.5/10/1.5 mol %) and a formulation of MC3/SPC-Chol conjugate/Chol/PEG-DMG at 42/3/53.5/1.5 mol % at N/P of 5, 6, 7, 8 and 9. The lipid nanoparticles encapsulate mRNA encoding luciferase. The N/P of the Onpattro™ formulation was 6.

As shown in FIGS. 8B and 8C, increasing the N/P of high sterol formulations (42/3/53.5/1.5 MC3/SPC-Chol/Chol/PEG-DMG (mol:mol)) did not have a substantial impact on activity (mRNA expression of luciferase) in the liver or spleen. Thus, the formulations can encapsulate a wide range of N/P without impacting liver tropism.

Example 7: Decreasing PEG-Lipid in High Sterol Formulations Improves Liver Targeting The inventors examined the in vivo expression of luciferase mRNA in both the liver and spleen with the LNP compositions of Table 2 below with varying levels of PEG-lipid. In particular, the high sterol LNP formulations examined included a four-component LNP having MC3/cholesterol/SPC-Chol/PEG-DMG at 42/55-X/3/X mol % of MC3/SPC-Chol/Chol/PEG-DMG in which X is 1.0, 1.5 or 2.0 mol %.

TABLE 2

LNP formulations prepared to examine liver vs spleen mRNA expression in vivo with varying levels of PEG-lipid conjugate

| Sample | LNP composition | Molar ratios | Cholesterol (mol %) | PEG-DMG |
|---|---|---|---|---|
| A | Onpattro ™ (MC3/Chol/DSPC/PEG-DMG) | 50/38.5/10/1.5 | 38.5 | 1.5 |
| B | MC3/Chol/SPC-Chol/PEG-DMG | 42/54/3/1.0 | 54.0 | 1 |
| C | MC3/Chol/SPC-Chol/PEG-DMG | 42/53.5/3/1.5 | 53.5 | 1.5 |
| D | MC3/Chol/SPC-Chol/PEG-DMG | 42/53.0/3/2.0 | 53.0 | 2.0 |

*SPC-Chol is a conjugate in which one acyl chain of DSPC is replaced with cholesterol (referred to as "H-001")

The LNPs were prepared as described in Example 2 above and in vivo studies to assess mRNA luminescence intensity in the liver and spleen were conducted using the procedure as described previously in Example 3.

Figure 9A:
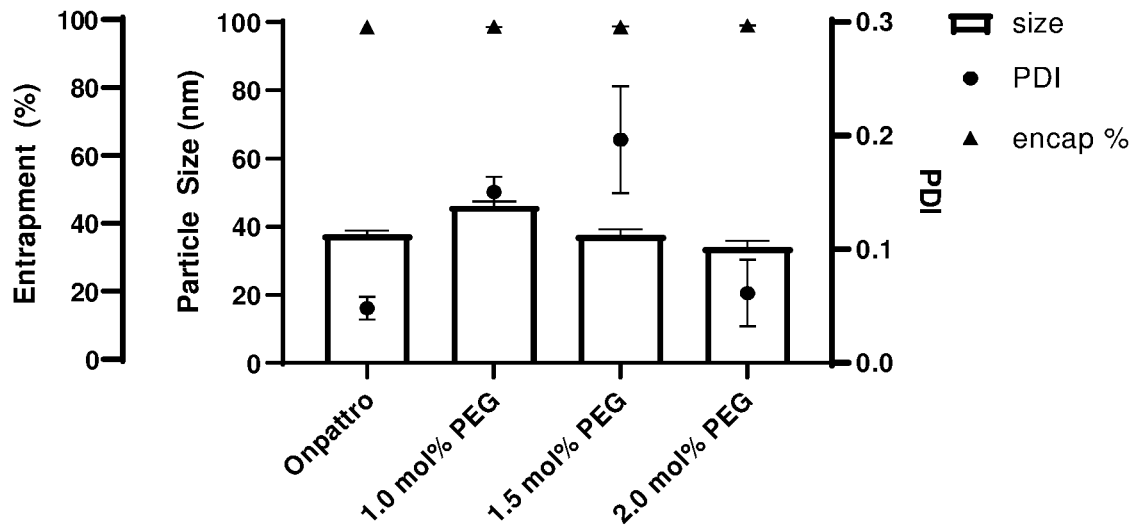
FIG. 9A is a graph showing entrapment (%), particle size (nm) and PDI of Onpattro™ (MC3/Chol/DSPC/PEG-DMG; 50/38.5/10/1.5 mol %) and three formulations of MC3/Chol/SPC-Chol/PEG-DMG having PEG-DMG contents of 1.0 mol % (42/54/3/1.0 mol:mol); 1.5 mol % (42/53.5/3/1.5 mol:mol) and 2.0 mol % (42/53.0/3/2.0). The lipid nanoparticles encapsulate mRNA encoding luciferase. The N/P of each formulation was 6.

The formulation characteristics including size (nm), PDI and encapsulation percent for each LNP were assessed as described in Example 1 and the results are presented in FIG. 9A.

Figure 9B:
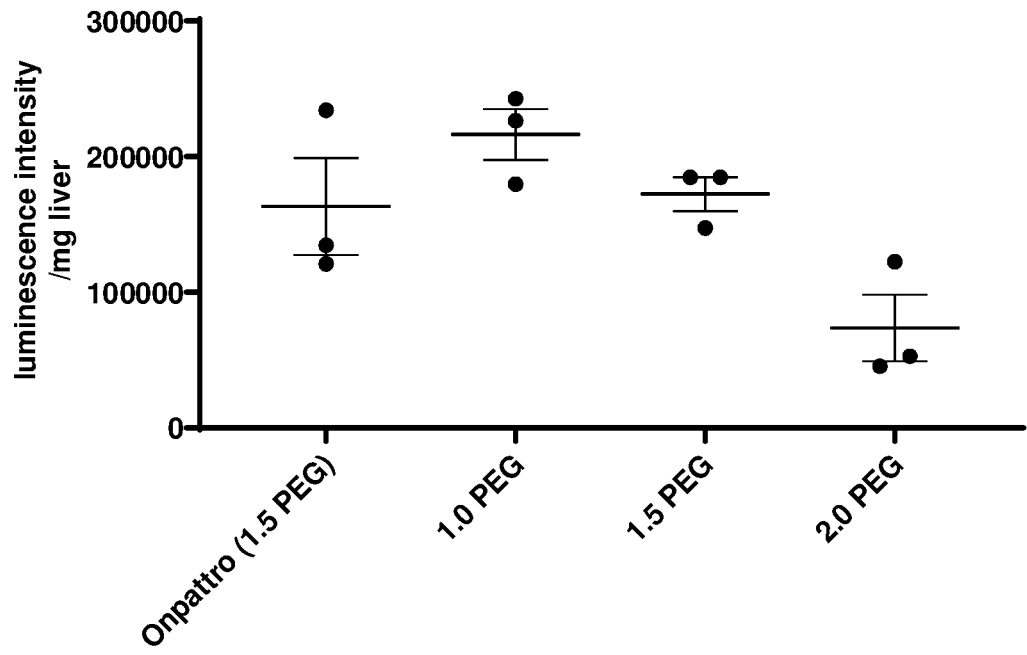
FIG. 9B is a graph showing in vivo luminescence of luciferase mRNA following liver extraction of CD-1 mice after treatment with mRNA luciferase-containing LNPs Onpattro™ (MC3/Chol/DSPC/PEG-DMG; 50/38.5/10/1.5 mol %) and three formulations of MC3/Chol/SPC-Chol/PEG-DMG having PEG-DMG contents of 1.0 mol % (42/54/3/1.0 mol:mol); 1.5 mol % (42/53.5/3/1.5 mol:mol); and 2.0 mol % (42/53.0/3/2.0). The lipid nanoparticles encapsulate mRNA encoding luciferase.

Decreasing the PEG-lipid mol % (Samples B-D in Table 2) in the high sterol formulations led to an increase in liver activity (see FIG. 9B). Surprisingly, the formulations having 1.0 and 1.5 mol % PEG lipid (Samples B and C in Table 2) exhibited higher levels of mRNA expression relative to Onpattro™ (Sample A of Table 2).

Example 8: A Variety of Different Ionizable Cationic Lipids are Capable of Formulation in High Sterol mRNA Lipid Nanoparticles and Improving Liver Tropism To determine the ability of a variety of different ionizable cationic lipids to be formulated in high sterol LNPs, formulations of ionizable cationic lipid/SPC-Chol/Chol/PEG-DMG at 42/2.7/54.3/1.0 mol % were prepared with the following ionizable cationic lipids having amino ionizable head groups: norMC3, C108, C109, C123, C124, C136, C137 and C142. The ability of the ionizable cationic lipids to improve liver activity vs Onpattro™ was investigated as well. The control was Onpattro™ (see Table 1 above).

The ionizable cationic lipids are set forth in Table 3 below.

TABLE 3

Ionizable cationic lipids used in high sterol formulations

| Ionizable cationic lipid | Citation (incorporated herein by reference) |
|---|---|
| nMC3 | WO 2022/246571 |
| C108 | U.S. 63/410,261 filed on Sep. 27, 2022 (compound 7) |
| C109 | U.S. 63/410,261 filed on Sep. 27, 2022 (compound 7 with ketal head group) |
| C123 | U.S. 63/434,506 (compound 9) |
| C124 | U.S. 63/434,506 (compound 11) |
| C136 | U.S. 63/434,506 (compound 14) |
| C137 | U.S. 63/434,506 (compound 7) |
| C142 | Ionizable cationic lipid with an amino alcohol head group and two branched tails with an ester group in each tail |

The LNPs were prepared as described in Example 2 above and in vivo studies to assess mRNA luminescence intensity in the liver and spleen were conducted using the procedure as described previously in Example 3.

Figure 10A:
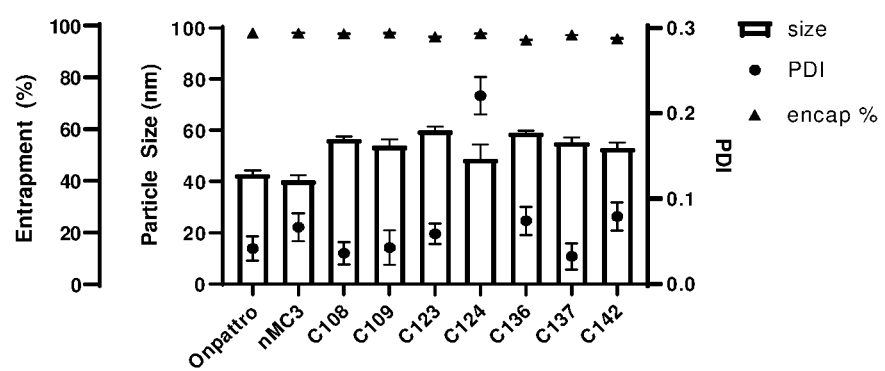
FIG. 10A is a graph showing physicochemical characterization of mRNA formulations showing entrapment (%), particle size (nm) and PDI of Onpattro™ (MC3/Chol/DSPC/PEG-DMG; 50/38.5/10/1.5 mol %) and formulations of ionizable cationic lipid/SPC-Chol/Chol/PEG-DMG at 42/2.7/54.3/1.0 mol %. The ionizable cationic lipids were norMC3, C108, C109, C123, C124, C136, C137 and C142 as described in Example 8.

The formulation characteristics including size (nm), PDI and encapsulation percent for each LNP were assessed as described in Example 1 and the results are presented in FIG. 10A.

Figure 10C:
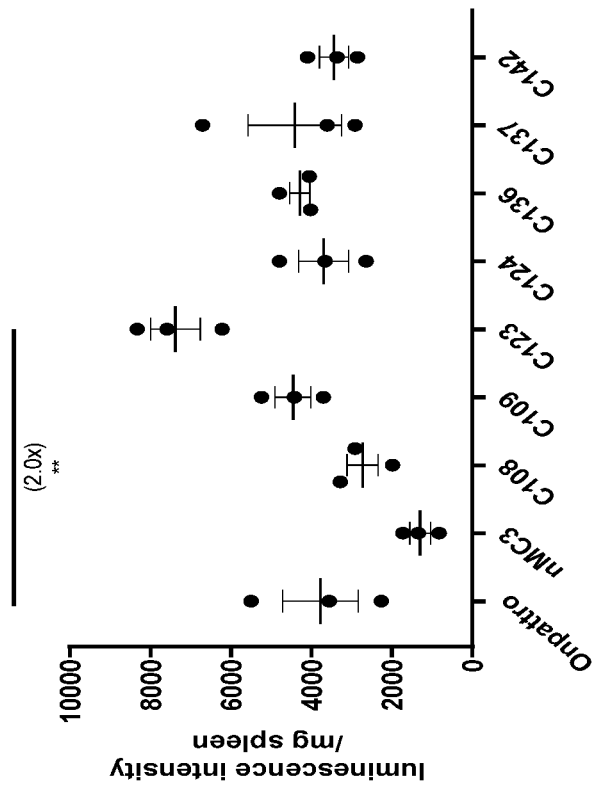
FIG. 10C is a graph showing in vivo luminescence of luciferase mRNA following extraction of spleen from CD-1 mice after treatment with mRNA luciferase-containing LNPs Onpattro™ (MC3/Chol/DSPC/PEG-DMG; 50/38.5/10/1.5 mol %) and high cholesterol formulations of ionizable cationic lipid/SPC-Chol/Chol/PEG-DMG at 42/2.7/54.3/1.0 mol % as described in Example 8.
Figure 10B:
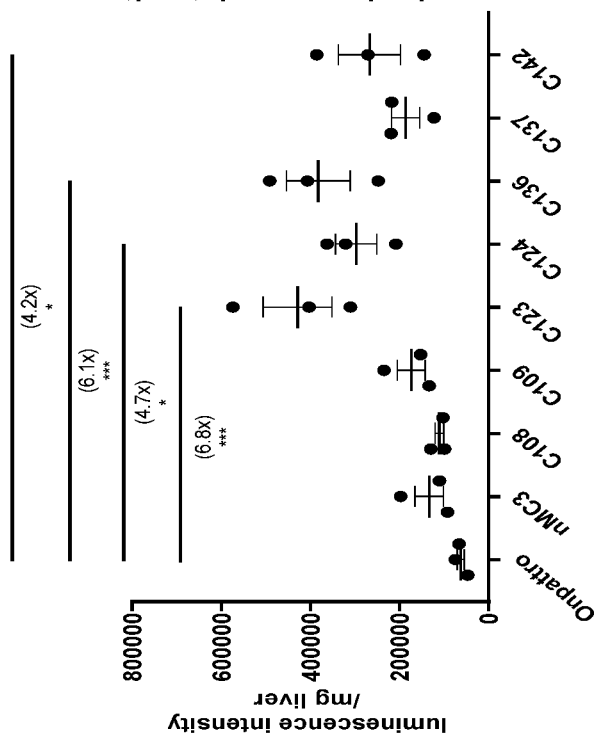
FIG. 10B is a graph showing in vivo luminescence of luciferase mRNA following liver extraction of CD-1 mice after treatment with mRNA luciferase-containing LNPs Onpattro™ (MC3/Chol/DSPC/PEG-DMG; 50/38.5/10/1.5 mol %) and high cholesterol formulations of ionizable cationic lipid/SPC-Chol/Chol/PEG-DMG at 42/2.7/54.3/1.0 mol % as described in Example 8.

Surprisingly, the formulations having ionizable cationic lipids with sulfur atoms in their lipophilic chains exhibited higher levels of mRNA expression relative to Onpattro™ (Sample A of Table 1). The liver activity was improved by 4.2 to 6.8 times for C123, 124, 136 and 143 ionizable cationic lipids (see FIG. 10B), while maintaining liver tropism as evidenced by low expression in the spleen (FIG. 10C).

Example 9: A Variety of Different Ionizable Lipids are Capable of Encapsulating Plasmid DNA in High Sterol Formulations and Improving In Vitro Transfection The ability of plasmid DNA to be encapsulated in a variety of high sterol LNPs with different ionizable cationic lipids was examined. In particular, formulations comprising ionizable cationic lipid/SPC-Chol/Chol/PEG-DMG at 42/2.7/54.3/1.0 mol % were prepared with the following ionizable cationic lipids having amino ionizable head groups: nMC3, C123, C124, and C136 (see Table 3 of Example 8 above for structures). The ability of the ionizable cationic lipids to improve in vitro transfection vs Onpattro™ was investigated as well. The control was Onpattro™ (see Table 1 above).

The LNPs were prepared as described in Example 2 above except with Aldevron Gwiz-Luciferase™ plasmid instead of luciferase mRNA and in vitro studies to assess luminescence intensity in Huh7 cells were conducted using the procedure as described previously in Example 2.

Figure 11A:
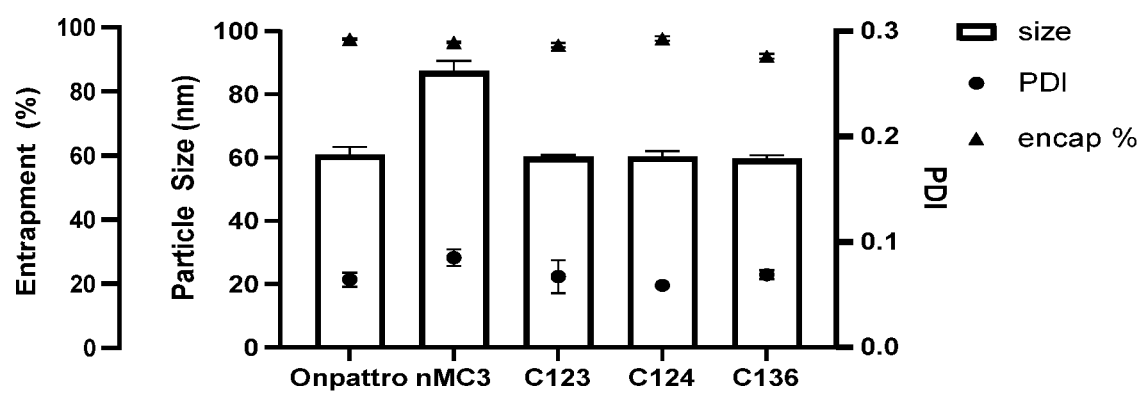
FIG. 11A is a graph showing physicochemical characterization of plasmid DNA formulations showing entrapment (%), particle size (nm) and PDI of Onpattro™ (MC3/Chol/DSPC/PEG-DMG; 50/38.5/10/1.5 mol %) and formulations of ionizable cationic lipid/SPC-Chol/Chol/PEG-DMG at 42/2.7/54.3/1.0 mol %. The ionizable cationic lipids were norMC3, C123, C124, and C136 as described in Example 8. The N/P ratio was 6.

The formulations characteristics including size (nm), PDI and encapsulation percent for each LNP were assessed as described in Example 1 and the results are presented in FIG. 11A.

Figure 11B:
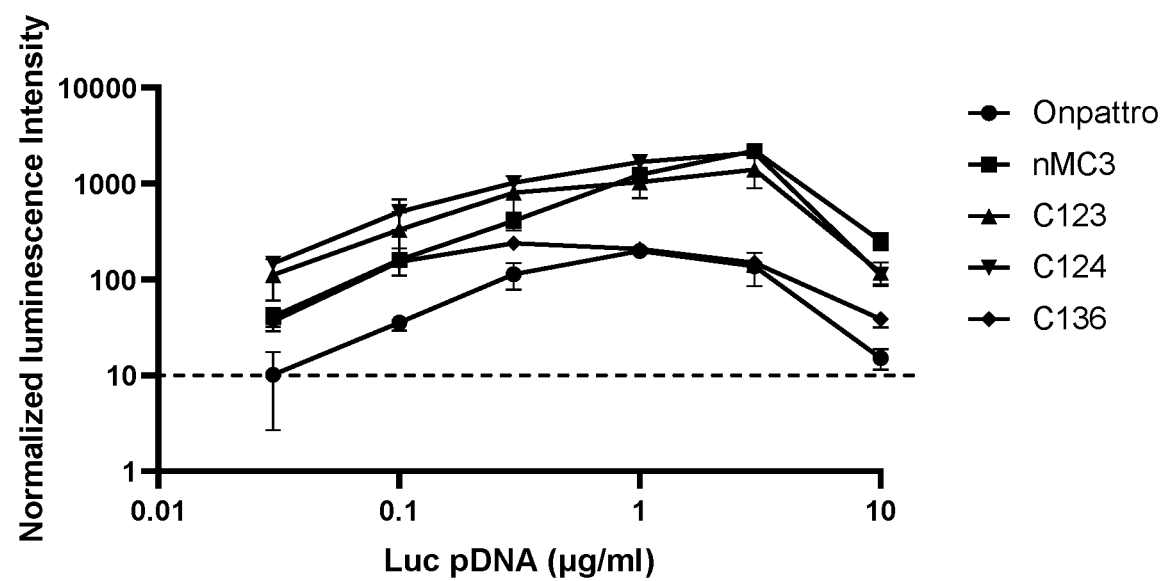
FIG. 11B is a graph showing in vitro luminescence as a function of plasmid DNA dose for Huh7 cells after treatment with ionizable cationic lipid (nMC3, C123, 124, and 136)/H-001/cholesterol/PEG-DMG LNP at molar ratios of 42/2.7/54.3/1.0 versus an Onpattro™ LNP formulation (50/10/38.5/1.5 of MC3/DSPC/cholesterol/PEG-DMG; mol/mol) encapsulating luciferase plasmid DNA. The N/P ratio was 6.

Surprisingly, the formulations having ionizable cationic lipids with sulfur atoms in their lipophilic chains exhibited higher levels of luciferase expression relative to Onpattro™ (Sample A of Table 1). The in vitro transfection activity was improved by 1.1 to 14.7 times at the same dose for nMC3, C123, 124, and 136 ionizable cationic lipids (see FIG. 11B).

Example 10: A Variety of Different Ionizable Cationic Lipids are Capable of Encapsulating siRNA in High Sterol Formulations The ability of siRNA to be encapsulated in high sterol LNPs formulated with a variety of different ionizable cationic lipids was examined. LNP formulations of ionizable cationic lipid/SPC-Chol/Chol/PEG-DMG at 42/2.7/54.3/1.0 mol % were prepared with the following ionizable cationic lipids having amino ionizable head groups: nMC3, C123, C124, C136 (see Table 3 in Example 8 for structures).

The LNPs were prepared as described in Example 2 above except with luciferase siRNA from Integrated DNA Technologies™ (IDT) instead of luciferase mRNA.

Figure 12:
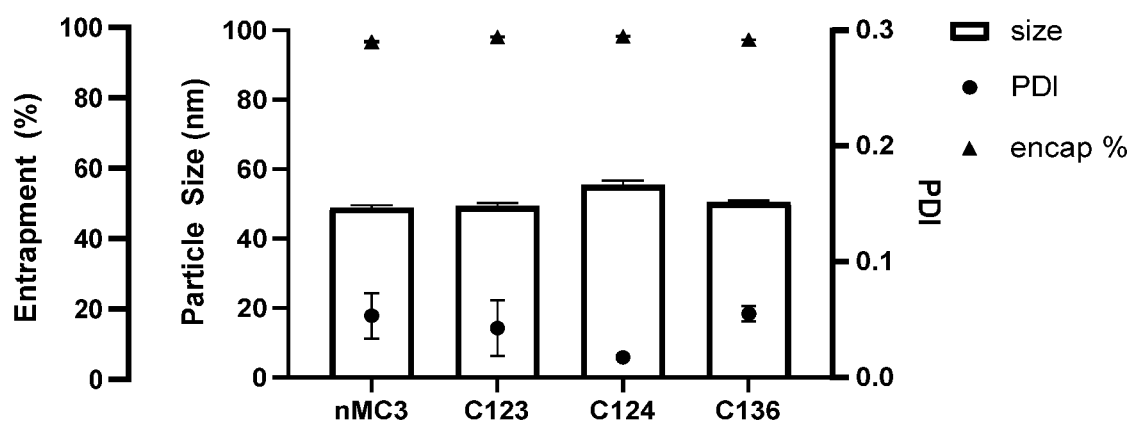
FIG. 12 is a graph showing physicochemical characterization of siRNA formulations showing entrapment (%), particle size (nm) and PDI of formulations of ionizable cationic lipid/SPC-Chol/Chol/PEG-DMG at 42/2.7/54.3/1.0 mol %. The ionizable cationic lipids were nMC3, C123, C124, and C136 as described in Example 8. The N/P ratio was 9.

The formulations characteristics including size (nm), PDI and encapsulation percent for each LNP were assessed as described in Example 1 and the results are presented in FIG. 12.

Example 11: High Sterol LNPs Exhibit Comparable Hepatic Cellular Specificity to Onpattro™, but are More Liver-Tropic To determine the cellular specificity of high sterol LNPs, mCherry mRNA was encapsulated within a high sterol LNP formulation of nMC3/SPC-Chol/Chol/PEG-DMG at 42/2.7/54.3/1.0 mol % in comparison with Onpattro™ (nMC3), in which CD-1 mice were injected at 1 mg/kg before mice were euthanized at a 24-hour end point. Mice were euthanized and perfused with 15 mL of cold 1× phosphate buffered saline (PBS). Livers were collected into 5 mL RPMI supplemented with 5% heat inactivated fetal bovine serum (HI-FBS). Livers were then minced and digested in RPMI with 0.5 mg/mL collagenase type IV (Sigma-Aldrich™) and 2 mg/mL DNase I (Sigma-Aldrich™) for 30 minutes at 37° C., with shaking at 200 rpm. Single cell suspensions were obtained by passing digested liver through a 70 μm sieve. Single cell suspensions were then spun at 50 g for 3 minutes at 4° C. to pellet and collect hepatocytes. The supernatant containing the non-parenchymal cell fraction was collected. Hepatocytes were then washed another two times with 10 mL flow cytometry staining buffer (FACS) buffer. The non-parenchymal fractions from livers were then isolated using a 20% OptiPrep™ gradient (StemCell Technologies™, see manufacturer's protocol). Cells were washed with FACS buffer and analyzed by flow cytometry (see below).

Surface Staining for Flow Cytometry

Liver cells were resuspended in PBS containing 5% HI-FBS, 0.05% $NaN_3$, and 2.5 mM EDTA (FACS buffer) and incubated with anti-FcgRII/RIII (2.4G2) for at least 15 minutes on ice. Cells were then stained with either fluorochrome conjugated against CD11b [M1/70], CD26[H94-112], CD31 [MEC13.3], CD38 [90], panCD45 [I3/2], CD45R (B220) [RA3-6B2], Clec4F [3E3F9], Ly6G [IA8], TCRP [H57-597] (Thermo Fisher™, BD bioscience, BioLegend) for 45 minutes on ice in the dark. To exclude dead cells, cells were stained with Fixable Viability Dye (Thermo Fisher™) as per manufacturer's instructions prior to flow cytometry acquisition.

Acquisition and Analysis of Flow Cytometry Data

A Cytoflex LX™ was used to obtain flow cytometry data, and analysis was performed using FlowJo™ (TreeStar™).

The LNPs were prepared as described in Example 2 above except with mCherry mRNA instead of luciferase mRNA.

Figure 13A:
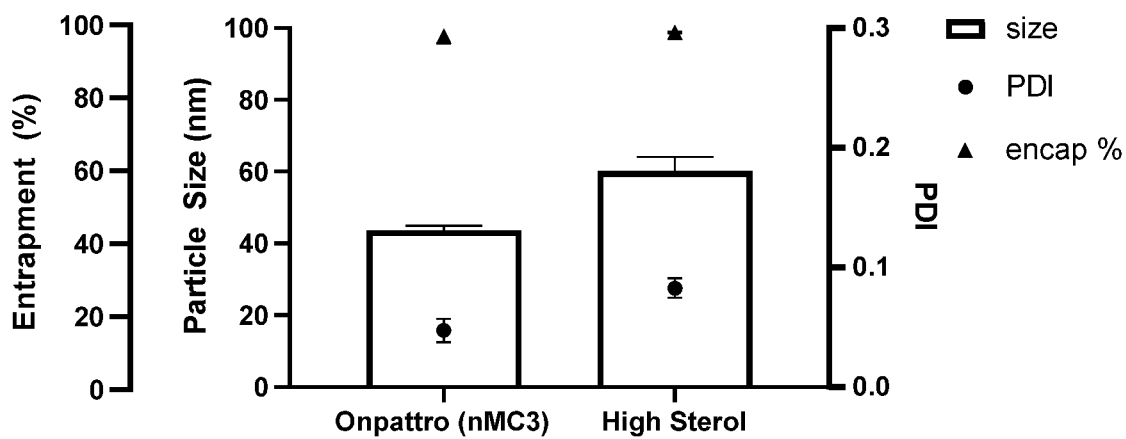
FIG. 13A is a graph showing physicochemical characterization of mRNA formulations showing entrapment (%), particle size (nm) and PDI of formulations of ionizable cationic lipid/SPC-Chol/Chol/PEG-DMG at 42/2.7/54.3/1.0 mol % and Onpattro™. The N/P ratio was 6.

The formulations characteristics including size (nm), PDI and encapsulation percent for each LNP were assessed as described in Example 1 and the results are presented in FIG. 13A.

Figures 13B, 13C:
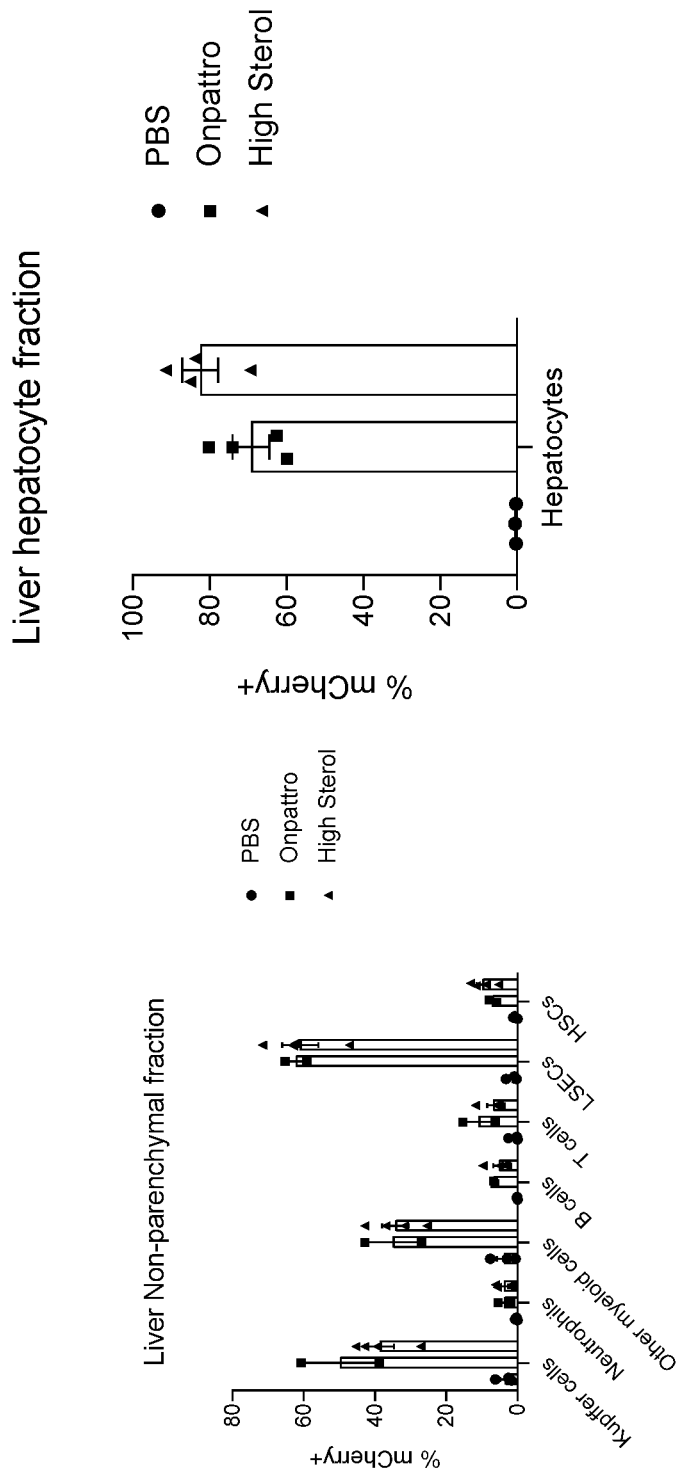
FIG. 13B is a graph showing percent mCherry uptake in various non-parenchymal cell types within the liver after treatment with nMC3/H-001/Cholesterol/PEG-DMG at molar ratios of 42/2.7/54.3/1.0 versus an Onpattro™ LNP formulation (50/10/38.5/1.5 of nMC3/DSPC/Cholesterol/PEG-DMG; mol/mol) encapsulating mCherry mRNA. The N/P ratio was 6.
FIG. 13C is a graph showing percent mCherry uptake in hepatocytes within the liver after treatment with nMC3/H-001/Cholesterol/PEG-DMG at molar ratios of 42/2.7/54.3/1.0 versus an Onpattro™ LNP formulation (50/10/38.5/1.5 of nMC3/DSPC/Cholesterol/PEG-DMG; mol/mol) encapsulating mCherry mRNA. The N/P ratio was 6.

Surprisingly, the high sterol formulations had comparable mCherry expression to Onpattro™ (with nMC3) in all cell types assessed (FIGS. 13B and 13C). Combined with the data presented in FIGS. 10B and 10C (Example 8), the results demonstrate a comparable formulation to Onpattro™ with the same ionizable lipid while increasing cellular tropism to the liver.

The invention claimed is:

1. A method for delivery of mRNA or vector DNA for in vivo production of protein or peptide in the liver, the method comprising administering to a mammal a lipid nanoparticle having 49 to 85 mol % of a sterol or a derivative thereof, a phospholipid or a phospholipid-sterol conjugate at 0 to 7 mol % that is in a neutral zwitterionic form at physiological pH, an ionizable lipid and a hydrophilic polymer-lipid conjugate present at 0.5 to 1.8 mol %, wherein the mRNA or vector DNA is encapsulated within the lipid nanoparticle and wherein the administering of the lipid nanoparticle results in liver-specific expression of the protein or peptide encoded by the mRNA or vector DNA, wherein the lipid nanoparticle has increased expression of the protein or peptide encoded by the mRNA or vector DNA in the liver over the spleen by at least 20-fold.

2. The method of claim 1, wherein the phospholipid or the phospholipid-sterol conjugate content is between 1 and 5 mol %.

3. The method of claim 2, wherein the phospholipid or the phospholipid-sterol conjugate content is between 1 and 3.5 mol %.

4. The method of claim 1, wherein the phospholipid or the phospholipid-sterol conjugate content is less than 7 mol %.

5. The method of claim 4, wherein the phospholipid or the phospholipid-sterol conjugate content is less than 6 mol %.

6. The method of claim 5, wherein the phospholipid or the phospholipid-sterol conjugate content is less than 5 mol %.

7. The method of claim 6, wherein the phospholipid or the phospholipid-sterol conjugate content is less than 4 mol %.

8. The method of claim 1, wherein the sterol or derivative thereof is present at 49 to 80 mol %.

9. The method of claim 8, wherein the sterol or derivative thereof is present at 49 to 65 mol %.

10. The method of claim 1, wherein the hydrophilic polymer-lipid conjugate is present in the lipid nanoparticle at a content between 0.5 and 1.6 mol %.

* * * * *